US012077761B2

(12) United States Patent
Valdivia et al.

(10) Patent No.: US 12,077,761 B2
(45) Date of Patent: Sep. 3, 2024

(54) SYSTEMS AND METHODS FOR GENETIC MANIPULATION OF *AKKERMANSIA* SPECIES

(71) Applicant: DUKE UNIVERSITY, Durham, NC (US)

(72) Inventors: Raphael Valdivia, Durham, NC (US); Per Malkus, Durham, NC (US); Lauren Davey, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 952 days.

(21) Appl. No.: 17/055,478

(22) PCT Filed: May 15, 2019

(86) PCT No.: PCT/US2019/032431
§ 371 (c)(1),
(2) Date: Nov. 13, 2020

(87) PCT Pub. No.: WO2019/222359
PCT Pub. Date: Nov. 21, 2019

(65) Prior Publication Data
US 2021/0222180 A1    Jul. 22, 2021

Related U.S. Application Data

(60) Provisional application No. 62/671,614, filed on May 15, 2018.

(51) Int. Cl.
*A61K 39/02* (2006.01)
*C12N 1/20* (2006.01)
*C12N 15/10* (2006.01)
*C12N 15/74* (2006.01)

(52) U.S. Cl.
CPC .............. *C12N 15/74* (2013.01); *C12N 1/20* (2013.01); *C12N 15/1079* (2013.01)

(58) Field of Classification Search
None
See application file for complete search history.

(56) References Cited

U.S. PATENT DOCUMENTS

| | | | |
|---|---|---|---|
| 7,595,048 | B2 | 9/2009 | Honjo |
| 8,008,449 | B2 | 8/2011 | Korman |
| 8,354,509 | B2 | 1/2013 | Carven |
| 8,728,474 | B2 | 5/2014 | Honjo |
| 8,779,105 | B2 | 7/2014 | Korman |
| 8,900,587 | B2 | 12/2014 | Carven |
| 8,952,136 | B2 | 2/2015 | Carven |
| 9,067,999 | B1 | 6/2015 | Honjo |
| 9,073,994 | B2 | 7/2015 | Honjo |
| 9,703,929 | B2 | 7/2017 | Apte |
| 2017/0306321 | A1 | 10/2017 | Valdivia |

FOREIGN PATENT DOCUMENTS

| | | |
|---|---|---|
| EP | 2170959 B1 | 4/2010 |
| WO | 1999/015650 | 4/1999 |
| WO | 2002016657 A1 | 8/2001 |
| WO | 2012061653 A2 | 5/2012 |
| WO | 2014075745 A1 | 5/2014 |
| WO | 2014201037 A1 | 12/2014 |
| WO | 2015095241 A2 | 6/2015 |
| WO | 2017/151811 A1 | 9/2017 |
| WO | 2018012834 A1 | 1/2018 |

OTHER PUBLICATIONS

Alam, A., et al. "The microenvironment of injured murine gut elicits a local pro-restitutive microbiota." Nature microbiology 1.2 (2016): 1-8.
Anhe, F. F., et al. "A microbial protein that alleviates metabolic syndrome." Nature medicine 23.1 (2017): 11-12.
Anhe, F. F., et al. (2015). Gut Microbiota Dysbiosis in Obesity-Linked Metabolic Diseases and Prebiotic Potential of Polyphenol-Rich Extracts. Current Obesity Reports, 389-400.
Bae, S., et al. "Genomic sequencing-based mutational enrichment analysis identifies motility genes in a genetically Intractable gut microbe." Proceedings of the National Academy of Sciences 113.49 (2016): 14127-14132.
Bastidas, R. J., et al. "Emancipating Chlamydia: advances in the genetic manipulation of a recalcitrant intracellular pathogen." Microbiology and Molecular Biology Reviews 80.2 (2016): 411-427.
Berer, K., et al. "Gut microbiota from multiple sclerosis patients enables spontaneous autoimmune encephalomyelitis in mice." Proceedings of the National Academy of Sciences 114.40 (2017): 10719-10724.
Cekanaviciute, E., et al. "Gut bacteria from multiple sclerosis patients modulate human T cells and exacerbate symptoms in mouse models." Proceedings of the National Academy of Sciences 114.40 (2017): 10713-10718.
Derrien, M., et al. "*Akkermansia muciniphila* gen. nov., sp. nov., a human intestinal mucin-degrading bacterium." International journal of systematic and evolutionary microbiology 54.5 (2004): 1469-1476.
Everard, A., et al. "Cross-talk between Akkermansia muciniphila and intestinal epithelium controls diet-induced obesity." Proceedings of the national academy of sciences 110.22 (2013): 9066-9071.
Everard, A., et al. "Responses of gut microbiota and glucose and lipid metabolism to prebiotics in genetic obese and diet-induced leptin-resistant mice." diabetes 60.11 (2011): 2775-2786.
Fuerst, J. A., et al. "Beyond the bacterium: planctomycetes challenge our concepts of microbial structure and function." Nature Reviews Microbiology 9.6 (2011): 403-413.
Goodman, A. et al. "Identifying microbial fitness determinants by insertion sequencing using genome-wide transposon mutant libraries." Nature protocols 6.12 (2011): 1969.
Guo, B.-S., et al. "Cloning, purification and biochemical characterisation of a GH35 beta-1, 3/beta-1, 6-galactosidase from the mucin-degrading gut bacterium Akkermansia muciniphila." Glycoconjugate journal 35.3 (2018): 255-263.

(Continued)

*Primary Examiner* — Jennifer E Graser
(74) *Attorney, Agent, or Firm* — Quarles & Brady, LLP

(57) ABSTRACT

The present disclosure provides methods and systems for genetically altering and screening *Akkermansia* bacteria, including *Akkermansia muciniphila*. The methods also provide genetically altered bacteria, libraries of genetically altered bacteria and use of such bacteria for treatment of diseases.

18 Claims, 6 Drawing Sheets

Specification includes a Sequence Listing.

(56) References Cited

OTHER PUBLICATIONS

Juang, K., et al. "Biochemical characterisation of the neuraminidase pool of the human gut symbiont Akkermansia muciniphila." Carbohydrate research 415 (2015): 60-65.

International Searching Authority. International Search Report and Written Opinion for application PCT/US2019/032431. Mailed on Sep. 17, 2019. 13 pages.

Jangi, S., et al. "Alterations of the human gut microbiome in multiple sclerosis." Nature communications 7.1 (2016): 1-11.

Koropatkin, N. M., et al. "How glycan metabolism shapes the human gut microbiota." Nature Reviews Microbiology 10.5 (2012): 323-335.

Levin, H. L. et al. "Dynamic interactions between transposable elements and their hosts." Nature Reviews Genetics 12.9 (2011): 615-627.

Liu, H., et al. "Magic pools: parallel assessment of transposon delivery vectors in bacteria." Msystems 3.1 (2018): e00143-17.

Ottman, N., et al. "Characterization of outer membrane proteome of Akkermansia muciniphila reveals sets of novel proteins exposed to the human intestine." Frontiers in microbiology 7 (2016): 1157.

Ottman, N., et al. "Genome-scale model and omics analysis of metabolic capacities of Akkermansia muciniphila reveal a preferential mucin-degrading lifestyle." Applied and environmental microbiology 83.18 (2017): e01014-17.

Plovier, H., et al. "A purified membrane protein from Akkermansia muciniphila or the pasteurized bacterium improves metabolism in obese and diabetic mice." Nature medicine 23.1 (2017): 107-113.

Routy, B., et al. "Gut microbiome influences efficacy of PD-1-based immunotherapy against epithelial tumors." Science 359.6371 (2018): 91-97.

Schneeberger, M., et al. "Akkermansia muciniphila inversely correlates with the onset of inflammation, altered adipose tissue metabolism and metabolic disorders during obesity in mice." Scientific reports 5.1 (2015): 1-14.

Semova, I., et al. "Microbiota regulate intestinal absorption and metabolism of fatty acids in the zebrafish." Cell host & microbe 12.3 (2012): 277-288.

Shin, N.-R., et al. "An increase in the *Akkermansia* spp. population induced by metformin treatment improves glucose homeostasis in diet-induced obese mice." Gut 63.5 (2014): 727-735.

Van Den Abbeele, P., et al. "Arabinoxylans and inulin differentially modulate the mucosal and luminal gut microbiota and mucin-degradation in humanized rats." Environmental microbiology 13.10 (2011): 2667-2680.

Wang, M., et al. "Cloning, purification and biochemical characterization of two β-N-acetylhexosaminidases from the mucin-degrading gut bacterium Akkermansia muciniphila." Carbohydrate research 457 (2018): 1-7.

The Akkermansia compatible transposon vector pSAM_Akk (SEQ ID NO:1)

SEQUENCE LISTING

```
<160> NUMBER OF SEQ ID NOS: 47

<210> SEQ ID NO 1
<211> LENGTH: 4476
<212> TYPE: DNA
<213> ORGANISM: Artificial Sequence
<220> FEATURE:
<223> OTHER INFORMATION: pSAM_Akk transposon vector
<220> FEATURE:
<221> NAME/KEY: bla_complement
<222> LOCATION: (1)..(861)
<220> FEATURE:
<221> NAME/KEY: KpnI
<222> LOCATION: (1072)..(1077)
<220> FEATURE:
<221> NAME/KEY: transposon
<222> LOCATION: (1078)..(2267)
<220> FEATURE:
<221> NAME/KEY: MmeI IR_L
<222> LOCATION: (1078)..(1106)
<220> FEATURE:
<221> NAME/KEY: inverted repeat left
<222> LOCATION: (1080)..(1107)
<220> FEATURE:
<221> NAME/KEY: MmeI_complement
<222> LOCATION: (1084)..(1089)
<220> FEATURE:
<221> NAME/KEY: BioSamA primer binding site
<222> LOCATION: (1102)..(1127)
<220> FEATURE:
<221> NAME/KEY: AscI
<222> LOCATION: (1127)..(1134)
<220> FEATURE:
<221> NAME/KEY: XhoI
<222> LOCATION: (1135)..(1140)
<220> FEATURE:
<221> NAME/KEY: MfeI
<222> LOCATION: (1141)..(1145)
<220> FEATURE:
<221> NAME/KEY: cat
<222> LOCATION: (1148)..(1960)
<220> FEATURE:
<221> NAME/KEY: terminator
<222> LOCATION: (1991)..(2034)
<220> FEATURE:
<221> NAME/KEY: terminator
<222> LOCATION: (2166)..(2193)
<220> FEATURE:
<221> NAME/KEY: BioSamA primer binding site
<222> LOCATION: (2218)..(2243)
<220> FEATURE:
<221> NAME/KEY: P7
<222> LOCATION: (2219)..(2238)
<220> FEATURE:
<221> NAME/KEY: inverted repeat right
<222> LOCATION: (2238)..(2265)
<220> FEATURE:
<221> NAME/KEY: MmeI IR_R
<222> LOCATION: (2239)..(2267)
<220> FEATURE:
<221> NAME/KEY: Bt1311 promoter
<222> LOCATION: (2274)..(2570)
<220> FEATURE:
<221> NAME/KEY: Himar codon optimized
<222> LOCATION: (2571)..(3628)
<220> FEATURE:
<221> NAME/KEY: RP4-OriT-OriR6K
<222> LOCATION: (3629)..(4428)
```

<400> SEQUENCE: 1

```
ttaccaatgc ttaatcagtg aggcacctat ctcagcgatc tgtctatttc gttcatccat      60
agttgcctga ctccccgtcg tgtagataac tacgatacgg gagggcttac catctggccc     120
cagtgctgca atgataccgc gagacccacg ctcaccggct ccagatttat cagcaataaa     180
ccagccagcc ggaagggccg agcgcagaag tggtcctgca actttatccg cctccatcca     240
gtctattaat tgttgccggg aagctagagt aagtagttcg ccagttaata gtttgcgcaa     300
cgttgttgcc attgctacag gcatcgtggt gtcacgctcg tcgtttggta tggcttcatt     360
cagctccggt tcccaacgat caaggcgagt tacatgatcc cccatgttgt gcaaaaaagc     420
ggttagctcc ttcggtcctc cgatcgttgt cagaagtaag ttggccgcag tgttatcact     480
catggttatg gcagcactgc ataattctct tactgtcatg ccatccgtaa gatgcttttc     540
tgtgactggt gagtactcaa ccaagtcatt ctgagaatag tgtatgcggc gaccgagttg     600
ctcttgcccg gcgtcaatac gggataatac cgcgccacat agcagaactt taaaagtgct     660
catcattgga aaacgttctt cggggcgaaa actctcaagg atcttaccgc tgttgagatc     720
cagttcgatg taacccactc gtgcacccaa ctgatcttca gcatctttta ctttcaccag     780
cgtttctggg tgagcaaaaa caggaaggca aaatgccgca aaaaagggaa taagggcgac     840
acggaaatgt tgaatactca tactcttcct ttttcaatat tattgaagca tttatcaggg     900
ttattgtctc atgagcggat acatatttga atgtatttag aaaaataaac aataggggt      960
tccgcgcaca tttccccgaa aagtgccacc tgacgtctaa gaaaccatta ttatcatgac    1020
attaacctat aaaaataggc gtatcacgag gccctttcgt cacgcgtcct cggtacctaa    1080
caggttggat gataagtccc cggtcttcgt atgccgtctt ctgcttggcg cgccctcgag    1140
caattgcgct cgtaagaggt tccaactttc accataatga aataagatca ctaccgggcg    1200
tattttttga gttatcgaga ttttcaggag ctaaggaagc taaaatggag aaaaaaatca    1260
ctggatatac caccgttgat atatcccaat ggcatcgtaa agaacatttt gaggcatttc    1320
agtcagttgc tcaatgtacc tataaccaga ccgttcagct ggatattacg ccttttttaa    1380
agaccgtaaa gaaaaataag cacaagtttt atccggcctt tattcacatt cttgcccgcc    1440
tgatgaatgc tcatccggaa ttccgtatgg caatgaaaga cggtgagctg gtgatatggg    1500
atagtgttca cccttgttac accgttttcc atgagcaaac tgaaacgttt tcatcgctct    1560
ggagtgaata ccacgacgat ttccggcagt ttctacacat atattcgcaa gatgtggcgt    1620
gttacggtga aaacctggcc tatttcccta aagggtttat tgagaatatg ttttttcgtct    1680
cagccaatcc ctgggtgagt ttcaccagtt ttgatttaaa cgtggccaat atggacaact    1740
tcttcgcccc cgttttcacc atgggcaaat attatacgca aggcgacaag gtgctgatgc    1800
cgctggcgat tcaggttcat catgccgttt gtgatggctt ccatgtcggc agaatgctta    1860
atgaattaca acagtactgc gatgagtggc agggcgggc gtaattttttt taaggcagtt    1920
attggtgccc ttaaacgcct ggtgctacgc ctgaataagt atgcgagagt agggaactgc    1980
caggcatcaa ataaaacgaa aggctcagtc gaaagactgg gcctttcgtt ttatctgttg    2040
tttgtcggtg aacgctctcc tgagtaggac aaatccgccg ggagcggatt tgaacgttgc    2100
gaagcaacgg cccggagggt ggcgggcagg acgcccgcca taaactgcca ggcatcaaat    2160
taagcagaag gccatcctga cggatggcct tttttgcgttt ctacctgcag ggcgcgccaa    2220
gcagaagacg gcatacgaag accggggact tatcatccaa cctgttagga tcctgatctg    2280
```

```
gaagaagcaa tgaaagctgc tgttaagtct ccgaatcagg tattgttcct gacaggtgta    2340
ttcccatccg gtaaacgcgg atactttgca gttgatctga ctcaggaata aattataaat    2400
taaggtaaga agattgtagg ataagctaat gaaatagaaa aaggatgccg tcacacaact    2460
tgtcggcatt ctttttttgtt ttattagttg aaaatatagt gaaaaagttg cctaaatatg    2520
tatgttaaca aattatttgt cgtaactttg cactccaaat ctgttttttaa catatggaaa    2580
aaaaggaatt tagggttttg ataaaatact gttttctgaa gggaaaaaat acagtggaag    2640
caaaaacttg gcttgataat gagtttccgg actctgcccc agggaaatca acaataattg    2700
attggtatgc aaaattcaag aggggtgaaa tgagcacgga ggacggtgaa cgcagtggac    2760
gcccgaaaga ggtggttacc gacgaaaaca tcaaaaaaat ccacaaaatg attttgaatg    2820
acaggaaaat gaagttgatc gagatagcag aggccttaaa gatatcaaag gaaagggttg    2880
gtcatatcat tcatcaatat ttggatatgc ggaagctctg tgcgaaatgg gtgccgcgcg    2940
agctcacatt tgaccaaaaa caacggaggg ttgatgattc aaagcggtgt ttgcagctgt    3000
taactaggaa tacacccgag ttttcaggc ggtatgtgac aatggatgaa acatggctcc    3060
atcactacac tcctgagtcc aatcggcagt cggctgagtg gacagcgacc ggtgaaccgt    3120
caccgaagag gggaaagact caaaagtccg ctggcaaagt aatggcctca gttttttggg    3180
atgcgcatgg aataatttttt atcgattatc ttgagaaggg aaaaaccatc aacagtgact    3240
attatatggc gttattggag aggttgaagg tcgaaatcgc ggcaaaacgg ccccacatga    3300
agaagaaaaa agtgttgttc caccaagaca acgcaccgtg ccacaagtca ttgagaacga    3360
tggcaaaaat tcatgaattg ggcttcgaat tgcttcccca cccgccgtat tcaccagatc    3420
tggcccccag cgactttttc ttgttctcag acctcaaaag gatgctcgca gggaaaaaat    3480
ttggctgcaa tgaagaggtg atcgccgaaa ctgaggccta ttttgaggca aaaccgaagg    3540
agtactacca aaatggtatc aaaaaattgg aaggtaggta ataggtgt atcgctcttg    3600
aagggaacta tgttgaataa gcggccgcca ccgcggtgga ggggaattcc catgtcagcc    3660
gttaagtgtt cctgtgtcac tcaaaattgc tttgagaggc tctaagggct tctcagtgcg    3720
ttacatccct ggcttgttgt ccacaaccgt taaaccttaa aagctttaaa agccttatat    3780
attctttttt ttcttataaa acttaaaacc ttagaggcta tttaagttgc tgatttatat    3840
taatttttatt gttcaaacat gagagcttag tacgtgaaac atgagagctt agtacgttag    3900
ccatgagagc ttagtacgtt agccatgagg gtttagttcg ttaaacatga gagcttagta    3960
cgttaaacat gagagcttag tacgtgaaac atgagagctt agtacgtact atcaacaggt    4020
tgaactgctg atcttcagat cctctacgcc ggacgcatcg tggccggatc aattccgttt    4080
tccgctgcat aaccctgctt cggggtcatt atagcgattt tttcggtata tccatccttt    4140
ttcgcacgat atacaggatt ttgccaaagg gttcgtgtag actttccttg gtgtatccaa    4200
cggcgtcagc cgggcaggat aggtgaagta ggcccaccccg cgagcgggtg ttccttcttc    4260
actgtccctt attcgcacct ggcggtgctc aacgggaatc ctgctctgcg aggctggccg    4320
gctaccgccg gcgtaacaga tgagggcaag cggatggctg atgaaaccaa gccaaccagg    4380
aagggcagcc cacctatcac ggaattgatc ccctcgaat tgacgcgtaa gggcagccca    4440
cctatcacgg aattgatccc cctcgaattg acgcgt                              4476
```

<210> SEQ ID NO 2
<211> LENGTH: 927
<212> TYPE: DNA
<213> ORGANISM: Akkermansia muciniphila

<400> SEQUENCE: 2

```
atgaagattc tcgtaaccgg cggcgccgga ttcatcggtt cccacattgt ggaacactat    60
caggataagg cggaggaaat ccgtgtgctg acaacctgc gcacgggcta tctcaagaac    120
ctggaagggc tcaggcacac gttcatcgaa ggttccatct cgaccgggga gctggtgcgc    180
caggcggtgc agggagtgga ctatattttc cacatggccg cgctcgtctc cgtgccggaa    240
tccatgagca agatcagcga atgcatcgac atcaacgtca acggtttgct gaacgtgctg    300
gaggaagctt ccgccgccgg agtcaaaaaa atcgtgctgg cgtcttccgc cgccatttac    360
ggagacaatc ccacggtgcc caaactggaa accatgtacc cggaacccaa gagtccctat    420
gccattacca agctggatgg ggaatactac ctcaacatgt ccgggcgga aggaaaaatt    480
aatacggcag ccgtgcgctt cttcaatgtc ttcggccccc ggcaggaccc caagggcgcc    540
tatgccgcag ccgtgcccat tttcattgaa aaagctgtca aggagaaga catcaccgtg    600
tatggggacg gctcccagac gcgcgatttc atttatgtga agacattgt aggagccctc    660
acctttgtgg cggaacaccc ggaagtcacc ggcgtgttca atgccggtta cggcggccag    720
atcaccattg aagagctggc gcagaacatc atcaaggctg ccgggtcttc ctccaaggtg    780
cttcatgccc cggaacgtcc gggagacgtc aagcattccc gcgcctgtgc ggacaagctc    840
cgcaatgccg gatggcagcc caggcatact ttgccggaag gcctggcgac gacgctggaa    900
tacttcaagg gcattctggg caggtaa                                        927
```

<210> SEQ ID NO 3
<211> LENGTH: 1290
<212> TYPE: DNA
<213> ORGANISM: Akkermansia muciniphila

<400> SEQUENCE: 3

```
atgttcccgt ttcctcctgt tgtccgttct ttcctgtttt ccctgtttga aagggcatgg    60
ctgagggctg cgttgtgctt ctgcctctgt acggcggtat gcgcctcctg ctccgtggac    120
aggcacatgg aaaaaaaggc gggggaattg atgccagga tggatgccgt tcccgattgg    180
cggcagctgc cgcggaagga aatctcatgg caccaggccc tggcgatgat gatggagcgg    240
aacattgact tgaaaaaatc ggagcagtcc ctcaagacga cgaaacgttc cgtcgttaat    300
gtttttaccc agattatccc cggagtcaat ctggactgga tgctgaccaa ggaattgagc    360
gacctggcca gggtgacggc cagcgatgtg aatacaata cgaacattct gttcaacatg    420
ccgtccctca cccagatccc gtttgattat tattccgcca aggcggctgt ttatacggcg    480
gaaaagacgc tggagatgaa aaaagggag ctggtggcca gattgtacca gcaggtgctt    540
tcctaccgga acgcgcagat cagctacaat aaccagctga gctccctgcc ttatgacgat    600
gatggcgtcc agaaaaagaa gctggacctg aacggggagc ggaatttgaa tgagatttcc    660
caggggtttg ccgtgttgct ggggaatatg acgcccgt ggctggtgaa ccctgaaacg    720
atgcccaggc tggactgggg caggtacagg gcggcgtccc ggcagctgga tctgctggtg    780
gtgacgatgg tggccatgga gctggaagct tcccgcctcc aggtgctgaa tgccaaactg    840
aagttcttcc cgtccgtgga tattaatttt tacagcccaa ccctgttttc cagcacgggc    900
gggacgtacg gcggttttt tgcgggagcg ggcgatatga aggtgaacat gagcctgcgg    960
gaagaactgg atacgcgcct gacatcctgg ttccagtata agtcggccaa agaaagccac   1020
gaactgctgc agcgcgaagt ggtgatggaa ctgcagcggg ggcgtatcaa gatagccgcg   1080
```

| | |
|---|---|
| ttgctggaga gccgcaggag gtttgagctc tggcaggggg tgctgatgaa ggaaatcgcg | 1140 |
| ttcaaggagt ccagattatc cgtttccgga gatgaatatc tggaacagag gaaggatatc | 1200 |
| aggaaaatgt atgctgacct ggataatgaa gcttccaaga atgcggaggt ggaagcggcc | 1260 |
| ctcatcatgg aatatggctg gctgaagtaa | 1290 |

<210> SEQ ID NO 4
<211> LENGTH: 759
<212> TYPE: DNA
<213> ORGANISM: Akkermansia muciniphila

<400> SEQUENCE: 4

| | |
|---|---|
| atgaaagtat cttttgcaac acaccagtta cgcaggggt ttaccctgat tgaactcttg | 60 |
| gttgtcattg ccattatcgc cctgctggct tccgtggcct atggtcctat cctgaaccag | 120 |
| atcaacaaag gcgaccagat gcaggccctg accaacatga gaacgtggg cgtagcgatg | 180 |
| aacgagttca atccaacag caaactgggc aatttccccg atgacatcac tgccgaccgc | 240 |
| gttgttgccc agcataatta tatgagcggc ctgggcgcac ttcagggcga tacttccaat | 300 |
| gactatttcc gtcagcttct gggcaatgag tctgtttccg aaagcaactt ttacgccaaa | 360 |
| gttcagactc cttccggcgg ttccaccgtt actcccaacg tgaaattta cgacggtcag | 420 |
| gccctgaccc ccggtgaagt gggtattttcc tacgtcatgc gcaagggtga caataacaag | 480 |
| aaagtgggta ttggaagttc cgtgggggaa tatccctga tggtcacttc cgtgcttcct | 540 |
| ggtgaagacg gcagcaccgt tgtggctggc aatgccgtgc gttttgaccc ggaaagcttc | 600 |
| cgcggcaagg ttctgatttt cacgactgcc cagagtgcca agaccctgga actggacgac | 660 |
| aacgacaacc ttcaggatac cttcattccc aagagaaggg gcaaggacat cagcgaccag | 720 |
| ttcctgatcc tcacgcctga tttcagcggc caggagtaa | 759 |

<210> SEQ ID NO 5
<211> LENGTH: 1023
<212> TYPE: DNA
<213> ORGANISM: Akkermansia muciniphila

<400> SEQUENCE: 5

| | |
|---|---|
| atggtattgg ccggactgtc ctccctggtt ccgtccatgg cccagaatgc ccagaatccc | 60 |
| cagcgcctgc gcgccagagt tgccgcaccg accatcaaga atggccgtcc gacggatatc | 120 |
| tacattctttt cctccaatgg acccacggtc cagtttgtgg agagcaggga atcccaggaa | 180 |
| gtccttcagc agatggccag cgccttcaag acgctgtata ttttgaaac ggacgacttt | 240 |
| gtggatgcca aggtggctat ggaaaaccgg aagtaccagg aagcccgcaa caaattccac | 300 |
| gctctggtga ataagtatgc ctcaacgctt tccatcaagg acagcctgtc cgcccgggcg | 360 |
| gccgtctatg aactggagtg cgccatgcgc atgatggatt gggctggagt caaagggttg | 420 |
| gcggccaagt ttcccgtcag aggggccaat ttgtcccctt ccgcccagaa tgacctggag | 480 |
| gtggcaaaaa tcatggcctt gattccagat aaggactgga acggcgtgaa aagccgtgcc | 540 |
| ggttcttttcc tggcaaccaa aaagaatgcc acccgcctcc agcaggcgcg gatgaaatat | 600 |
| gccctgggtg cggccgccat ggtggcccag gattggaaca aggcgctgga ttattttgcg | 660 |
| gaagccctgg ttttgttgca tggttccgat gaagaactgg cgtctgcctg cgtggcccgc | 720 |
| tcccctggatg cctacctgcg catgccggat gttgtcaaat ctttgagaa tcccgtcgtc | 780 |
| tcatctgccg tggaatccag gaagaataat cccgaagctg tgattccgga ttcacggctg | 840 |
| aagtcccgtc cgttcctgt caaggaagcg gctgccctgt accgtttgca tgaactgatg | 900 |

| | | |
|---|---|---|
| ttcccggaca ggaagctgcc ggccaagtat gacggttttg cggtttccta caagcatccg | 960 | |
| gccgctgttg ctcccgccaa ggctcctgac caggctcccg cacagccgca gaataagcag | 1020 | |
| taa | 1023 | |

<210> SEQ ID NO 6
<211> LENGTH: 3234
<212> TYPE: DNA
<213> ORGANISM: Akkermansia muciniphila

<400> SEQUENCE: 6

| | |
|---|---|
| atgatcaaat caaactatac tactgcactg gctgcaggcc tggtttccgt gctgagtatc | 60 |
| ggggcggttc ttccatccgg cgcccagcat ggcccgcgcg attaccagcg cacggccctg | 120 |
| acggccatta aggaagggaa gtggcaggaa gccctggatg ccgtggatcg ctgcatccgc | 180 |
| gtttatgaac cccgtatcaa gatgctgggg ctggatgacg gcttcggctg gttctattac | 240 |
| cagaagggcg tctgtctggc ccagctgaaa aattacaagg aggctgtgga agcgttcaag | 300 |
| gcttgttaca ccaagtttcc gagcgctaaa aaccagctcg tgaaaatggc cctgttccgg | 360 |
| gaaggggaaa actactgccg tcttggggat tttgccaagg gtgcggagct gctgaaaaaa | 420 |
| ttcctgaaag aataccgcag cgatcctgtc gccagaaacg tcaatgctgg cgaagtgcag | 480 |
| gggcttctgg cccaatgcta tttcaagatg tctccgcctg cttttgaaaa agggatggaa | 540 |
| aaccttacct cttgcgtcac gtcacgctac aagggccgcc gcattacgga tgccgttatt | 600 |
| accaatggct ttctggcgat ggtggatgcc gccattaaga ccggcaaatg cagtgagacg | 660 |
| gtgaagtttg tggaaaacta cccttccgtg atgaatatca gtcccacgcg tgtggctttg | 720 |
| tacaccccgc ggctggtgag ctacgttgcg gaagtgctgg agaaatcccg ttccctgctt | 780 |
| caggatggaa agcagaaaga gtctgaagat tatgcttccc tggcgatggt gctgatgggt | 840 |
| cttcttcccg atcagtccgg agtaatggcg gatgccaatt attccctgga tcgtctgggc | 900 |
| cgtgccaacg gggccgtgcc tggcgtgacg gattttttcc atacgctgga cagagcgaag | 960 |
| gtgacggccc tgatcgacca gttcaacaag atgaaggagg aaggaaaggt catggacgcc | 1020 |
| ttcacgttca gctttatggg caaccaggcc ctggtgcatg gttcccaaag ggttgcccgc | 1080 |
| gccgcctacc agcttatcaa tgaatcctac ccggatgctc cgggcaggga ggataacctg | 1140 |
| tattatctgg cgatgaccac ctggcagctg ggagaagcgg acaagggagg cgagcttgtg | 1200 |
| gcgcagcacc tgaaggaatt ccccaattcc aagtatgccc ccatgcttaa tacgctgtct | 1260 |
| ttggaagggc ttctgaagga aaaaaaattc gatctctgcg ttcagcaggc ggacaaggtc | 1320 |
| atggagttgc ataaggatga ccccaccat aagttctatg aactggcct gtactgcaaa | 1380 |
| ggagcctccc tgttcaacct gggggctgcc gacgcctccc gttataagga agcggtgccg | 1440 |
| gtgctggaac gcttcgtgaa ggaataccgt gacagcactt atctgaaaac ggccatgtac | 1500 |
| cttcttggtg aaacctacac gaacctgggc aatacggatg aagccatccg gtcctttacc | 1560 |
| aattacattg cccgtttccc ggacaagggg gaggccaata tggccgccgt attgtatgac | 1620 |
| cgggccttca actacctgaa ccgcaagaac cccggagacg aagagcttgc cgcgaaagat | 1680 |
| gcgaaggaaa ttgtggacaa tttcaaggac caccgcctgt tcccgtatgc caacaatttg | 1740 |
| ctggctaatc tgtgtgccgg cagcaaggag catgagcagg aagcggaagg ctatttcctg | 1800 |
| gccgctctgg agtccgccaa gaagctgggc gacaagcgtc ccgctgcgga agccgtgtac | 1860 |
| aacctgtttta ttaacgctac caagaagcct cttccggtag aaccgaagga agccgtggaa | 1920 |

-continued

| | |
|---|---|
| acggccagga cggcgcgccg ggacgaggtc aagaaatggt atgacgagta ctggaaagac | 1980 |
| agcgaccagc ccggcagccg ctacagcctc cagctggctg ccgccgccat ggacttcttt | 2040 |
| aaggatgaca aggagatgtt tgacccggca tccgtcaaga tgcaggaaat tattgtgagg | 2100 |
| gaaggcaaga aggacgatcc caagatgacc gttcttctgg aagaggccgt caattcctat | 2160 |
| accaagacgt acatggccgg caatcaggcc ctgggccgca atctggatgc caatgccatg | 2220 |
| cgcaaccact tctaccggtt ccccggcgtg acaatgata aagacaagac gctgagcgcc | 2280 |
| atgcttcgca tggccgttat tgcccagact caggaacggt atgaaaaggc tcctgtggag | 2340 |
| acggacgaac agcgtgccga aaagccgcc ctggaaggtc tggtcaagca gctcttcgtg | 2400 |
| gagctgaagc gcgacttcaa gccttccgat ctgccccgt acacgcttgt gaagcttggc | 2460 |
| atgcacctgg ccggcacttc ccagcctgaa gaaagcatct cctactttga tgaaatcctg | 2520 |
| gacccgtcgg aacctgaccc ggtgcgtaag aaggcccgca tcaacggcat gtccaagtac | 2580 |
| cgcaagaatg cggtcttcgg gaaagccgta gctctggggc gcagcaagga taacgccaag | 2640 |
| gtggacaccg ccatcaagat gatgagggat gaactgagca aggaagaatc cagctccaac | 2700 |
| ccggaccgca aggccatgga agacgcccag tacaatctgg tcaagttcac ttccgcccgc | 2760 |
| caggactggc cggccgtcat tgccgctgcc gacaagtacc gcgaaaacaa gacctataag | 2820 |
| aagaatctgc cggaagtcct ctatctgcag ggtgaagcct acctgaagca gaatgagctg | 2880 |
| gacaaggcgt tgattaactt catgaacatc acgggtacgt acaaggggct cgtgaagtgg | 2940 |
| tccgccccg ccgtgctggc gcagatggat acgctgtgga agaggaatac gatgtcccag | 3000 |
| ggtgcgggca agcagccttc cgacaggtac gttgcctgga aggccggcag ccagtacgtg | 3060 |
| cagttgctgg atactcccgc caaccgcaag aagatgacgg cggaggacag tgccctggtc | 3120 |
| aatgaggtga aggataagac ggccaagttc ggttccgatc ctgccgtcag ccaggaacgg | 3180 |
| gcggacattg ccgcctatga agcagccgta cgcgccgcca agggccagaa ataa | 3234 |

<210> SEQ ID NO 7
<211> LENGTH: 1785
<212> TYPE: DNA
<213> ORGANISM: Akkermansia muciniphila

<400> SEQUENCE: 7

| | |
|---|---|
| ttatttgtta aagttcacgg gaatgggcgt tttaacgga agcaccagct tgaagggtac | 60 |
| aaaggcccct gccgccgcgt ccaccttggc gtccttggct cccagttcca tgatctggcg | 120 |
| ggcttccagt ttgacgtctc cgggcttgaa agtgaacagg gattccttgt tcccgtctat | 180 |
| ttttgcctgg aggtcctgga tgattctctg gccgcccagg ctgcgccgga cgaatccggt | 240 |
| caggcggatg gcgttgacgc tgtaaacgcc gcttcatcc tcgctggatg cgttggcgga | 300 |
| ggcctccgtc ctgatgtcat ccaccaggga tgtattttg tccgatgtga aggaatcctt | 360 |
| gatgacggaa tatcccgtaa tttgggtggt atcctccgga ttgaagtggg ccagcggttc | 420 |
| aaaatccgta accagtagg gataatcctt gtgttccgac tgttccagca ggtgcctgat | 480 |
| gatgtccgcg tagccgtagc gctgaagcgt gagctgctgg taggaagcca gggtggagtc | 540 |
| cagttttttc agctcctgtt ctttctggcg cagggcggat tgtgccgatt tgatggaagt | 600 |
| aacggtgggc tggacgccgg cgaggatttc ctccgccttt ttctcgccca tatatcctgt | 660 |
| gacggcataa gctgcggcac caagaacggc aatggctgcc ccggcgatga tgcgggcat | 720 |
| tttttctgg ttggcccgct ttttggcaac tgcggtgggt tccaggtcaa tattgaggga | 780 |
| ggccctgccg atggagtgaa tggcggtgcc gatcaatccg cccaggatga aggcttcgcg | 840 |

```
ggagatggtg ttcacgtcca cgccggagcc cacgcccacg ttgtgcatgg ggttgaagaa        900
ggagatcgga atgcccagtt tatcttccag gaattccttg gtatagggca gggaagctcc        960
gccgccgcac aggtatgcct tgacgggagc gcttccgctc atctgggcgc ggtaatggtt       1020
ggtggtccgc tggatttctg aggcaagcct ggtcatggcc gtacgatga cggtagccag        1080 attggccgtg gcgggatcca gcccttccgt ttgcccgttg ctcatggaaa cgagcccgct       1140
ggtggttttc aagcgttccg cttccaggaa gggaatattg aattcacggg cgatagcgga       1200
ggttacgaag attcccccg cggaaatgct gcgggtgaag aaacgtccct gttcgctgta        1260
aatcaaatcc gtggatttgg cgccgatgtc gatgagcatg accggttctt tctcatccgg       1320
ataactgtcc acatacgcat tgtacagaga ggtaagcgcg cagtccactt gccggtgga        1380 aaggccgtgg agacgatttt catcattcag ggagtccagg tcttccgcct tgatggcaac      1440
caggatggct tcccgttcca gacctttggc gggaagcaga tggtagtccc cacgacttc       1500 gtccagcggg aaggggacgt gctgctgggc ttcaaagcgg atgagctgtt ccacatcggt      1560
atcgtccaga gccggaagct tgacgaagcg gatgaaaacg gattgtccgg aaacggaata     1620
gttgacgacg cttcctttga cgttgagttc ctggacgagg tcggcgatgg cttcccctat     1680
tttcgtcagg cgcaaacctt ctgctgacgg gtccagcact acgaggcgcg tagcatagcg    1740
gtccaggata agggcgtctt tggaagtctt ggaaaagacg cccat                       1785

<210> SEQ ID NO 8
<211> LENGTH: 717
<212> TYPE: DNA
<213> ORGANISM: Akkermansia muciniphila

<400> SEQUENCE: 8
atgaaatcca tccttaacac tatcacggcc atgctggctg cggtgctttt cgtccctgcg         60
gcatcggcgc agaccaccag caatcccaga atgcaggtgc gggtctccct ggaaaagctg        120
tccctgtata tgcgccagtc ccccaacgtc ctgacgcagg acgatcccg gccgctgccg         180 aaaccgaaga aatgggcgga ttttgaaatt cccttcaagg tggaagccgc tcccacccc         240 aaatccggct atattgatgc cctgacgttc aaattctaca tcgcggtagt caatccggac       300
cgctcccgcc agtatctgaa actgtataag gaagtcaaat acgtcaatgt tccggtagga      360
gaaaacacgt acgcttccgt gtatctctcc ccgtcctccg tcaagcgcat taccggtgtg    420
gaaggaggaa gaggaaaatg ggtgaagtac cagggcgtag tggtggaata caacggcaag     480
attgtcgcca cttattcctc cgaacgcggc aaaatggaaa atggtggac catccagtcc       540 cccagcatcg tggagaccctc ttattacccc ctgctgaaca aggatgaaac tcctttctcc     600
gtgttctggt acgaccgtta tccggaaatt atgaggccca acagccagca ggcggcttcc     660
agttccgtcc ccgccccgtt cggtactcct gtggaacctc cggcggacgg cgaataa        717

<210> SEQ ID NO 9
<211> LENGTH: 777
<212> TYPE: DNA
<213> ORGANISM: Akkermansia muciniphila

<400> SEQUENCE: 9
atgtgggtca agtatcaat agcagccttg gtcattgctc ttctcggagg agccatgtat          60
tatcttgata cgaggaagc tctaaccaag gagcgtaggg aatgtgcttc ccgctacaag        120
aacctgaacg gccttcgtgg cgaatttacg gaagaaaaga cgaaatatgt cgatttcctg       180
```

```
gtgaagaatg aggctctgac gaatgacatc aatgctttaa ccaaggagaa ggatgaactg      240
gaagtaaaga atcaggaatt ggcctcagcc aatgaggcca agaaatctga ccttcaaacg      300
cagcaaaccg ctttggcgga attgcaatcc aagagtaagg atatggaaag tatccaagcc      360
attgctgaca gaatcaaggg gctggaagaa gagtccaagc agttggaagt ggttaagcag      420
gcggaacagg aaaacatga tgccatcgtc gctgaaactg aacagcttgt tgtgaataat      480
gccgctcttc gtcagctcaa ggccgaccag gatgcccgcc tttctccgcc caacctgaaa      540
acgagggttt cccaggtgat tcatgatttt aatgtagttg tgattgacgg aggagccgcc      600
gatctgggcg tggtgcccgg ttccaagttg gccgtcatga gggacggcaa caaaattgcc      660
gagcttgacg taaacgctgt tgaatcccgt gttccacgg ccactattct accaagtacg       720
gtaaccgccg gcgaacgtgt tgaagccgga gacgtcgttg tatctgttcg tccctag        777

<210> SEQ ID NO 10
<211> LENGTH: 1248
<212> TYPE: DNA
<213> ORGANISM: Akkermansia muciniphila

<400> SEQUENCE: 10
atgagccttc atatagaacc cacggaagac gcagtggaaa ccctgcgcaa ggaaaggcgg       60
aaaaattata ttgccgcatt agcgacatcc attctctccg tcgttttggc aggagccatt      120
ctctactccc tgaccatcat catcgcccct ccggaagaac ccaaagtcgt cggctacatc      180
acgccggacg atgcgccgcc gtcggatacg cctccgccgc cggaagtaca gagggaaact      240
tcctcttcct cccatgcgga gacgcccgtc aaggtcgtgg tggcagcggc cgccgctccg      300
gtgagcctcc ccaagatcga cattgacccg cccgatgaac ctgtcatgct ggaggaggga      360
accgccctcg gcatggggga cggcttcggc cccgacctgg gagacgctac ctccgccttt      420
ggtacgtcca aaccctccgg aagcacgctg gtaggtacct tttacgacac caagcagact      480
cctggcggac gtcctaccaa catgaacatg aaccagtaca gggagttcct ttcccgcttc      540
gtgaacaaag gctggaacga atcggaactg aaccgttttt acaaggctcc gcaacaatta      600
tacgcagccc agttctacat acctaggact cccgccaaag acgctcccaa ggcctacggt      660
tgcgatgaca agtaaagcc tagccagtgg ctcgccattt accggggaaa agtacgcgcc       720
cccaagtccg gcacgttccg attcgtgggg ttgggagacg actacttagt agtacggttc      780
aataaacaga atgtcttcga ctacggctgg gaatccgctt ctctgggaa atgacggca        840 aacaacgcca atggcttga tgccatgaa ggcaaacccg gcaatgacga cttgaaaaag        900
gaactccggg aagtgggcat caatgtcccc cccgttacgt tctacaaata cagttcttcc      960
gggcactgga caacactat gcgcggtgtg gcagccggca agcagttcac ggtgaacag       1020 ggcaaggttt accccattga atcctagtt agtgaaggtc ctggtggcga attcggcatg     1080
actcttctgc ttgaagaagt tggaatggcc cccatgagca aggatcctaa acgggagct      1140 cccatcctgc cctgttccg aaccaactac ggcgttccga aaccggacaa gaacaaggaa     1200
cacgtgccat ttgacgaaat cggcattgtc tgggaatcca tcaaataa                1248

<210> SEQ ID NO 11
<211> LENGTH: 1383
<212> TYPE: DNA
<213> ORGANISM: Akkermansia muciniphila

<400> SEQUENCE: 11
atgattgaaa cgattacaga agaacagttg actccccagc aggccgaatt ttgggtgcgc       60
```

```
gcccgccagg cggtggacat gaacaattat ccctatgccg tcagcctgct caaggccctg      120
gtaaagcagc tccccggttt tctggaaggc cgcaaggcgt tgcgcgcctg tgaaatcaaa      180
ttgaatccgg aggccaagag agggggggctg ttcagcggta tgaaaatcag caccagcaag     240
ctcacttctt ccaagaagga cgcggctacc cagctttccg ctctggaaga cgaattggaa      300
aatgatcctt acagcattcc ggtaaacgag gccctgtaca cggctgccat ggaagtaaat      360
ttcccggatc tggccgcttt tgctctggag accgttcgcc aggggcatcc cggcaacaag      420
aaaatgctcc acatgctggc ctcccattac gttttcccggg atatgccggc ccaggctgcg     480
gaagtgtacc atgaccttgt gaagctggat cccacggaca gtgtggccgt aaagagcgaa      540
aaggactgca tggcgcgcgc cacgatgcag cagcagaagt gggaggaggc taaaagcttc      600
cgggacgtga tgaagaactc gtcggaaacg aacaccctgg acaagagcga caagaaaggg      660
ctcacccgtg cggaactgga agagcgcctg gggcttctct ccgcccgtta cgcccagaac      720
cagcaggatc tggccgtcgt gcgcgacatt gccggcgttt atgaacaaat ggaagattgg      780
gccaatgcct attccttcta taattacgcg ttcagcctca gcaacaatga tatttccctg      840
gaaaacaagg cctcggaaat gaatgagcga tgccgcaagg cccaggtgga ggaaatccgc      900
cgccgcgctg ccgcggagcc ggataataag gaacttcagg aacagcttgc ccagttcagc      960
aaggaagctg cggagcagca ggtggccttg tgccgcagc gtgtggaaaa caaccccacg      1020
gacccgcaaa cccgttttga gctgggccag gccctcttcg actgcggcaa ttacacggaa     1080
gccattccgg aactccagcg cgcccgcaac aatccccata tccgcatccg cgccatgctg     1140
ttgctcggca agtgctatga cgccaagaac atgcatgata tggctctgcg ccagctggag     1200
gaagccaata aggaattgat agaaatgaat gacaccaaga aggaaatcct ttacatgatc     1260
ggcttgcttt tgtgaaaagca gggcaagaag ggggaatccc tggctgcatt ccagcagatt    1320
tacgacgccg agtacggcta ccgcgacgta gccaggcgcg tggaatcctc ttacggcaat    1380
tag                                                                    1383

<210> SEQ ID NO 12
<211> LENGTH: 462
<212> TYPE: DNA
<213> ORGANISM: Akkermansia muciniphila

<400> SEQUENCE: 12
atgttcaaca tcgtgagatt caccaggcgt acctgtccgg cattggccct cacgctggcc      60
cttacttcgt gcgacagcag tacgaatgaa gccctgacct ccttcctgac ggggaattca     120
tcccaggaac accagcagct ccaggcccag ctccagcaaa tgaaaaacgc actggcccag     180
acggaacagg aaataagcca ggcggaatcc cacgatgccc gcgttaatta caatcttcag     240
aaaaggcttt ccaacccggg aagaatcacg acgcccttca cggtgaagga tatagatgtc     300
ctgccttcca aacgccgcga cttcgagcac ctgtgctttg acattgaaga catgcgcaaa     360
acgctggcgc agcgcaagca ggaattccat gccctgcaat atcaatataa cgcgtatgcg     420
gccaaactgg ctgaattcaa acaaacccac ccggtagact aa                        462

<210> SEQ ID NO 13
<211> LENGTH: 747
<212> TYPE: DNA
<213> ORGANISM: Akkermansia muciniphila

<400> SEQUENCE: 13
```

| | | |
|---|---|---|
| atgccaaaaa tcgttgttca atcctgcatc atctgtatga gatattttc caagcattcc | 60 | |
| ggaatggctc cgcgctgttc ctcgccgggg agcaaggggt ttaccctggt ggaattgatt | 120 | |
| gtcgttatca ccattatggt tgccatgatg gccttggccg ccagcatgtt gagggggggg | 180 | |
| ggcaggggc aggggcttca ggccgccgtt gaaatggtgg acggcatggt gcaggaggcg | 240 | |
| cggctggatg ccatgggcaa aggaacgtgg agccgcctga ttattgtgag cactcccgat | 300 | |
| gacgaagccc gcaatatgcg cactttgggc gtgatgtcca aaaatacccg caccgggaaa | 360 | |
| tggcatctgg tgaaccgttt gcagactctc cccgccggtt tttacgtcag tccggcctac | 420 | |
| agcacccttc tggaaggctc gaagaaagcc agaggcgaga atccacggc cgcggttt | 480 | |
| gccagccgtg acgggcagga taccgtcaac cttcccggca acagaatgac ggatatttac | 540 | |
| ttcattgaat ttgacgagga aggccgcatg tcccagccga acgccccac ccgcctggtg | 600 | |
| gtggttgccg gttccgccgg aaacggcaag gaggagaggc cgaccccgat ggtggacggc | 660 | |
| aaaccgggcc tggcaggcgg cattgtgatt tatcccaaag gcaatatcag ccgtctgagg | 720 | |
| acgacggagc aggtgattcc caattag | 747 | |

<210> SEQ ID NO 14
<211> LENGTH: 801
<212> TYPE: DNA
<213> ORGANISM: Akkermansia muciniphila

<400> SEQUENCE: 14

| | | |
|---|---|---|
| atgttgacca agtgtatgaa acagtctcgt gccaagggt tcaccctgac ggaagtggtg | 60 | |
| cttgcgatcg gcgtggtggc cgtgctgatt gtagtgttca tggccatgtt tattcctgcc | 120 | |
| agaaggacgg ttcagtccgc cctgactatt cgtgaagcgg accgcatcgt ccacgccctg | 180 | |
| acggcggaac ttggagaact ccgcaattcc gagcgtgccg cgtccaacgc cagaaagtct | 240 | |
| tcctcctcca gatatgttc cgcttttgac aaggcgtttt actggatgca gttcacgtcc | 300 | |
| aggcccgcta cgaccattct tgtttacaat tacaggggcgg attgaccaa gggggcccgc | 360 | |
| aaagacggaa ctccccagcc ctggctggag gatggcggaa gcattcccgg caaaaatact | 420 | |
| gcggtggtga caggggtctg cctggcgaac aacaaagagc gttgggatga tttcaaggcc | 480 | |
| cttgtcggtc ccgtcttcgc cgtgcgcatg acccagctgg tagtggagcg catggattca | 540 | |
| agctcctacg ggtacaagct ggctcccaag tacgggacga tttataatcc ttacaaccgc | 600 | |
| ggcaaggtga ttaaggaacc ttccctgtat gtttatacgc cggagaaagg cggcggcctg | 660 | |
| aatttgccgt gggggggcgga agtcctgtac caggcggagt tcttccagct gttgaatacg | 720 | |
| gaccccgagc gtttacaaca tctgacgtgg gaaaatttaa agactcccgt gtttacgcgc | 780 | |
| aatctcgctt ccgccgtta g | 801 | |

<210> SEQ ID NO 15
<211> LENGTH: 759
<212> TYPE: DNA
<213> ORGANISM: Akkermansia muciniphila

<400> SEQUENCE: 15

| | | |
|---|---|---|
| atgaaagtat cttttgcaac acaccagtta cgcagggggt ttaccctgat tgaactcttg | 60 | |
| gttgtcattg ccattatcgc cctgctggct tccgtggcct atggtcctat cctgaaccag | 120 | |
| atcaacaaag gcgaccagat gcaggccctg accaacatga gaacgtggg cgtagcgatg | 180 | |
| aacgagttca atccaacag caaactgggc aatttccccg atgacatcac tgccgaccgc | 240 | |
| gttgttgccc agcataatta tatgagcggc ctgggcgcac ttcagggcga tacttccaat | 300 | |

| | |
|---|---|
| gactatttcc gtcagcttct gggcaatgag tctgtttccg aaagcaactt ttacgccaaa | 360 |
| gttcagactc cttccggcgg ttccaccgtt actcccaacg gtgaaattta cgacggtcag | 420 |
| gccctgaccc ccggtgaagt gggtatttcc tacgtcatgc gcaagggtga caataacaag | 480 |
| aaagtgggta ttggaagttc cgtgggggaa tatcccctga tggtcacttc cgtgcttcct | 540 |
| ggtgaagacg gcagcaccgt tgtggctggc aatgccgtgc gttttgaccc ggaaagcttc | 600 |
| cgcggcaagg ttctgatttt cacgactgcc cagagtgcca agaccctgga actgacgac | 660 |
| aacgacaacc ttcaggatac cttcattccc aagagaaggg gcaaggacat cagcgaccag | 720 |
| ttcctgatcc tcacgcctga tttcagcggc caggagtaa | 759 |

<210> SEQ ID NO 16
<211> LENGTH: 3234
<212> TYPE: DNA
<213> ORGANISM: Akkermansia muciniphila

<400> SEQUENCE: 16

| | |
|---|---|
| atgatcaaat caaactatac tactgcactg gctgcaggcc tggtttccgt gctgagtatc | 60 |
| ggggcggttc ttccatccgg cgcccagcat ggcccgcgcg attaccagcg cacggccctg | 120 |
| acggccatta aggaagggaa gtggcaggaa gccctggatg ccgtggatcg ctgcatccgc | 180 |
| gtttatgaac cccgtatcaa gatgctgggg ctggatgacg gcttcggctg gttctattac | 240 |
| cagaagggcg tctgtctggc ccagctgaaa aattacaagg aggctgtgga agcgttcaag | 300 |
| gcttgttaca ccaagtttcc gagcgctaaa accagctcg tgaaaatggc cctgttccgg | 360 |
| gaagggaaa actactgccg tcttggggat tttgccaagg gtgcggagct gctggaaaaa | 420 |
| ttcctgaaag ataccgcag cgatcctgtc gccagaaacg tcaatgctgg cgaagtgcag | 480 |
| gggcttctgg cccaatgcta tttcaagatg tctccgcctg cttttgaaaa agggatggaa | 540 |
| aaccttacct cttgcgtcac gtcacgctac aagggccgcc gcattacgga tgccgttatt | 600 |
| accaatggct ttctggcgat ggtggatgcc gccattaaga ccggcaaatg cagtgagacg | 660 |
| gtgaagtttg tggaaaacta cccttccgtg atgaatatca gtcccacgcg tgtggctttg | 720 |
| tacaccccgc ggctggtgag ctacgttgcg gaagtgctgg agaaatcccg ttccctgctt | 780 |
| caggatggaa agcagaaaga gtctgaagat tatgcttccc tggcgatggt gctgatgggt | 840 |
| cttcttcccg atcagtccgg agtaatggcg gatgccaatt attccctgga tcgtctgggc | 900 |
| cgtgccaacg gggccgtgcc tggcgtgacg gattttttcc atacgctgga cagagcgaag | 960 |
| gtgacggccc tgatcgacca gttcaacaag atgaaggagg aaggaaaggt catggacgcc | 1020 |
| ttcacgttca gctttatggg caaccaggcc ctggtgcatg gttcccaaag ggttgcccgc | 1080 |
| gccgcctacc agcttatcaa tgaatcctac ccgatgctc cggcaggga ggataacctg | 1140 |
| tattatctgg cgatgaccac ctggcagctg ggagaagcgg acaagggagg cgagcttgtg | 1200 |
| gcgcagcacc tgaaggaatt ccccaattcc aagtatgccc ccatgcttaa tacgctgtct | 1260 |
| ttggaagggc ttctgaagga aaaaaaattc gatctctgcg ttcagcaggc ggacaaggtc | 1320 |
| atggagttgc ataaggatga ccccacccat aagttctatg aactggccct gtactgcaaa | 1380 |
| ggagcctccc tgttcaacct gggggctgcc gacgcctccc gttataagga agcggtgccg | 1440 |
| gtgctggaac gcttcgtgaa ggaataccgt gacagcactt atctgaaaac ggccatgtac | 1500 |
| cttcttggtg aaacctacac gaacctgggc aatacggatg aagccatccg gtcctttacc | 1560 |
| aattacattg cccgtttccc ggacaagggg gaggccaata tggccgccgt attgtatgac | 1620 |

| | |
|---|---|
| cgggccttca actacctgaa ccgcaagaac cccggagacg aagagcttgc cgcgaaagat | 1680 |
| gcgaaggaaa ttgtggacaa tttcaaggac caccgcctgt tcccgtatgc caacaatttg | 1740 |
| ctggctaatc tgtgtgccgg cagcaaggag catgagcagg aagcggaagg ctatttcctg | 1800 |
| gccgctctgg agtccgccaa gaagctgggc gacaagcgtc ccgctgcgga agccgtgtac | 1860 |
| aacctgtttta ttaacgctac caagaagcct cttccggtag aaccgaagga agccgtggaa | 1920 |
| acggccagga cggcgcgccg ggacgaggtc aagaaatggt atgacgagta ctggaaagac | 1980 |
| agcgaccagc ccggcagccg ctacagcctc cagctggctg ccgccgccat ggacttcttt | 2040 |
| aaggatgaca aggagatgtt tgacccggca tccgtcaaga tgcaggaaat tattgtgagg | 2100 |
| gaaggcaaga aggacgatcc caagatgacc gttcttctgg aagaggccgt caattcctat | 2160 |
| accaagacgt acatggccgg caatcaggcc ctgggccgca atctggatgc caatgccatg | 2220 |
| cgcaaccact tctaccggtt ccccggcgtg gacaatgata agacaagac gctgagcgcc | 2280 |
| atgcttcgca tggccgttat tgcccagact caggaacggt atgaaaaggc tcctgtggag | 2340 |
| acggacgaac agcgtgccga gaaagccgcc ctggaaggtc tggtcaagca gctcttcgtg | 2400 |
| gagctgaagc gcgacttcaa gccttccgat ctgcccccgt acacgcttgt gaagcttggc | 2460 |
| atgcacctgg ccggcacttc ccagcctgaa gaaagcatct cctactttga tgaaatcctg | 2520 |
| gacccgtcgg aacctgaccc ggtgcgtaag aaggcccgca tcaacggcat gtccaagtac | 2580 |
| cgcaagaatg cggtcttcgg gaaagccgta gctctggggc gcagcaagga taacgccaag | 2640 |
| gtggacaccg ccatcaagat gatgagggat gaactgagca aggaagaatc cagctccaac | 2700 |
| ccggaccgca aggccatgga agacgcccag tacaatctgg tcaagttcac ttccgcccgc | 2760 |
| caggactggc cggccgtcat tgccgctgcc gacaagtacc gcgaaaacaa gacctataag | 2820 |
| aagaatctgc cggaagtcct ctatctgcag ggtgaagcct acctgaagca gaatgagctg | 2880 |
| gacaaggcgt tgattaactt catgaacatc acgggtacgt acaaggggct cgtgaagtgg | 2940 |
| tccgccccg ccgtgctggc gcagatggat acgctgtgga agaggaatac gatgtcccag | 3000 |
| ggtgcgggca gcagccttc cgacaggtac gttgcctgga aggccggcag ccagtacgtg | 3060 |
| cagttgctgg atactcccgc caaccgcaag aagatgacgg cggaggacag tgccctggtc | 3120 |
| aatgaggtga aggataagac ggccaagttc ggttccgatc ctgccgtcag ccaggaacgg | 3180 |
| gcggacattg ccgcctatga agcagccgta cgcgccgcca agggccagaa ataa | 3234 |

<210> SEQ ID NO 17
<211> LENGTH: 1659
<212> TYPE: DNA
<213> ORGANISM: Akkermansia muciniphila

<400> SEQUENCE: 17

| | |
|---|---|
| atggacacca acctcacact ggaacttttc atcggccggg gaatgattga caaatccctg | 60 |
| gcaaaggaca tcaaggagga aatgatcgcc tccggcaagg agctgccgga agtgcttgca | 120 |
| gacttcggca tcatcggcag caaggatgat atctggcaga tgattgccag cgacctgggt | 180 |
| acggaattca ttacactgga caacttccag ccggatccga acgtgcagaa catgatgccg | 240 |
| gccacgctcg tgcgcctgca cggggcgctc cctgtgcggc atggtccgga aggcctgtac | 300 |
| gtctgcctgg tggatcccct gaatcccag acggtggaag acctgcgctt cgccctcggc | 360 |
| caggacatcc atgttctggt agcgccggat taccagattt ccgaacgcat caatgagctt | 420 |
| tatgagggcg aatccgccgc catgtccgac ctgatgcagg agctgaacaa catgcaggtc | 480 |
| aacaatgaga cggaggactc cgccgccgct cccgtcatcc gctttgtgga cctcgtcatt | 540 |

| | | |
|---|---|---|
| acgcaggcca tcaaggaaaa ggcctccgac attcacttcg aaccttttga gaaggaattc | 600 |
| aaaatccgct accgtgtgga cggcgccctg tatgaaatgc agcctccccc cgtccacctg | 660 |
| tccgtgccgg tcatttcccg cgtcaaagtc atggcgaaca tgaacatcgc ggaacgccgc | 720 |
| attccgcagg acggacgcat cgtcaagcag ataggaaacc gttccgtgga catgcgcgtt | 780 |
| tcctcccttc ccactcagta cggagaatcc gtggtgctcc gcgttctgga ccgctcttcc | 840 |
| gtcaacttga acatggacaa cctggggctt cccgcgcata tccacgaata tattctggat | 900 |
| acggtccaca agcccaacgg catttttcatc gttaccggcc ccaccggcgc cggcaagaca | 960 |
| actacgctgt atgccgccct gcgtgaaatc aataccattg attccaaggt gctgacggcg | 1020 |
| gaagaccctg ttgaatacga tattgacggc atcatccaga ttcctatcaa tgaagccatc | 1080 |
| ggcctggact tcccaatggt gctccgcgcc ttcctgcgac aggacccgga ccgtattctg | 1140 |
| gtgggggaaa tgcgagacat ggcaacagcg cagatcgcca tccaggcatc cctgacgggt | 1200 |
| cacctggttc tctccaccct gcacacgaac gactccgccg gagccattac gcgactggtg | 1260 |
| gacatgggat gcgaaccttt cctggtggcg gcttccctgg aaggggtgct tgcacagcgc | 1320 |
| ctggtgcgca ccatctgtcc ggactgccgc acgccgtatg aaccctcatc caccatcctc | 1380 |
| tcccagcttg gcgtctctcc ctatgaactg ggagacaagc acttttttcac gggccgaggc | 1440 |
| tgtgataaat gctccaattc cggctacagg ggccgcaagg ggatttatga gctcctggat | 1500 |
| attaacgata ccctgcgcga catgattacg gatcgcgctc cttccgtggt gctgaagcag | 1560 |
| aaagccattg aaatgggcat gtccacgctg cgggaagacg ggctgagaaa tatttatgac | 1620 |
| ggcaacacca ccattgaaga agtgctgaaa tatacttaa | 1659 |

<210> SEQ ID NO 18
<211> LENGTH: 1269
<212> TYPE: DNA
<213> ORGANISM: Akkermansia muciniphila

<400> SEQUENCE: 18

| | | |
|---|---|---|
| atgcctaaat atcaatacac agcacttgac cataaaggcg accagaaaac aggtaccctg | 60 |
| gaggccaatt ccgaagcgga ggccatggaa tccatccggg cgcatggcct gtaccccacc | 120 |
| cagatcgtag aagcgggcaa gggcaagatt cagcagacgc ctgccgccaa gaaaaaggcc | 180 |
| aagggagcca agaagcaaaa aggcaagctg ggaggcaaaa tcaaggccaa ggctctgatg | 240 |
| attttcaccc gccagcttgc tacgctgatt gacgcggggc ttcccctgct ccagagtttg | 300 |
| aacgtgctgg ccaaacagga ggcaaacccc aactgcgcg taaccattga ggctcttgga | 360 |
| gattccgttc agggcggctc caccttctcg gaagccctgg cccaacaccc cagaattttt | 420 |
| gaccgcctgt ttgtcaacat ggtaaaggcc ggggaactgg gcggtgtgct ggaagtcgtg | 480 |
| ctgaaccgtc tggcggaata ccaggaaaag gcccaaaagc tgaaaagcaa ggtgatctcc | 540 |
| gccatggtgt atccctccat cgtcctgttt atcgccgtag catcgtgat cttcctgatg | 600 |
| ctggtcatcg tgcccaaatt caaggcgatg ttcgcagaac agaaccagga acttcccggt | 660 |
| atttccgagt ttgtgttcgg catcagcgac tggttcatgg ccgcccccctt ctttgtgccc | 720 |
| aatgccgtca ttctggccgc ggtagtcgcc atcctgtacg ctgttttcac ggccatgagc | 780 |
| aagacgccca acggacgccg caagattgac tccgctctgc tgaccatgcc ggtcatcggc | 840 |
| aatgtgcaga gcaaaagcgc catcgcccgc ttcgcccgaa ccttcggtac gctggtgact | 900 |
| tccggcgtcc ccatcctcca ggcgcttacc atcacgaagg ataccgccgg caacatgatc | 960 |

| | | | |
|---|---|---|---|
| gtgggagacg | ccatcggcct | catccatgac tccgtcaagg | aaggcgaatc cgtagttacg | 1020 |
| cccatgtcct | cctccaagct | tttcccgccc atggtaatct | ccatggtgga cgtgggggaa | 1080 |
| gaaaccggcc | agttgccgga | catgctcctg aaaatcgcgg | acgtgtatga tgatgaagtg | 1140 |
| gacaatgccg | tgggagctat | gacctccatg ctggaaccca | tcatgatcgt attcctggcc | 1200 |
| gtggtcgtgg | gcggcatcgt | gttcgccatg ttccttcccc | tcctgcaggt tattgaaaag | 1260 |
| atgggataa | | | 1269 |

<210> SEQ ID NO 19
<211> LENGTH: 717
<212> TYPE: DNA
<213> ORGANISM: Akkermansia muciniphila

<400> SEQUENCE: 19

| | | | | |
|---|---|---|---|---|
| atgaaatcca | tccttaacac | tatcacggcc | atgctggctg cggtgctttt | cgtccctgcg | 60 |
| gcatcggcgc | agaccaccag | caatcccaga | atgcaggtgc gggtctccct | ggaaaagctg | 120 |
| tccctgtata | tgcgccagtc | ccccaacgtc | ctgacgcagg acgatcccg | gccgctgccg | 180 |
| aaaccgaaga | atgggcggga | ttttgaaatt | cccttcaagg tggaagccgc | tcccaccccc | 240 |
| aaatccggct | atattgatgc | cctgacgttc | aaattctaca tcgcggtagt | caatccggac | 300 |
| cgctcccgcc | agtatctgaa | actgtataag | gaagtcaaat acgtcaatgt | tccggtagga | 360 |
| gaaaacacgt | acgcttccgt | gtatctctcc | ccgtcctccg tcaagcgcat | taccggtgtg | 420 |
| gaaggaggaa | gaggaaaatg | ggtgaagtac | cagggcgtag tggtggaata | caacggcaag | 480 |
| attgtcgcca | cttattcctc | cgaacgcggc | aaaatggaaa aatggtggac | catccagtcc | 540 |
| cccagcatcg | tggagacctc | ttattacccc | ctgctgaaca aggatgaaac | tcctttctcc | 600 |
| gtgttctggt | acgaccgtta | tccggaaatt | atgaggccca acagccagca | ggcggcttcc | 660 |
| agttccgtcc | ccgccccgtt | cggtactcct | gtggaacctc cggcggacgg | cgaataa | 717 |

<210> SEQ ID NO 20
<211> LENGTH: 984
<212> TYPE: DNA
<213> ORGANISM: Akkermansia muciniphila

<400> SEQUENCE: 20

| | | | | |
|---|---|---|---|---|
| atggacaccc | gagaattcaa | cgaaattatc | gccgcgaact catcgtggat | ttctgctctc | 60 |
| agaacggaag | tcggcaaggt | ggtcatcggc | cagcaggcgc tcgtggacag | attaatcctc | 120 |
| agtctcctct | gcaagggcca | cgtcctgctg | aaggcgtgc ccggccttgc | caagacgctc | 180 |
| tccgtaaaag | ccatggcggg | cacgctgcat | gcacagtttg cccgcatcca | gtttacgccg | 240 |
| gatcttcttc | cggcggattt | gctgggcaca | atgatctata tccggaaga | aaggcagttc | 300 |
| acagccaaaa | aaggcccgat | cttcgccaat | ctcattttgg cggatgaaat | caaccgcgcc | 360 |
| ccggccaaag | tgcaatccgc | cctgctgaaa | gccatgcagg aacgccaggt | aaccctaggt | 420 |
| gaaaccacct | accgcctgcc | ggacccctct | ctggtgcttg ccacgcagaa | cccgattgac | 480 |
| caggagggca | cttaccagct | cccggaagcc | cagcttgacc gttttctctt | caaggtgctg | 540 |
| gtcacctacc | ccacgcgcga | agaagaactc | caggtgctgg acctcatggc | cagctccgcc | 600 |
| aaaccgccgg | aaacctcccc | ggtcaccacg | ccggaacagg tggcggcctc | ccgcgacctg | 660 |
| gtaaaccaga | tttatattga | cgacgccgtg | cgcggctaca tcgtggatct | ggtgcgcgcc | 720 |
| acccgcttcc | cggaaacggt | ggacgtgaag | ttgcgcggtc tcatccgcgc | ggggggcatct | 780 |
| ccccgcgcta | ccatcaacct | ggctctggcg | gcccgcgcca atgccttcat | gcaccatcgt | 840 |

```
tccttcgtca ctccacagga tatcaaggac ctggcccacg atatcctgcg ccaccgcatc    900
ctgctctctt atgaggctga agcggaaaac atttccacgg acgacgtcat cgaccacatc    960
ctgacgaaag tccccgtgcc gtga                                           984
```

<210> SEQ ID NO 21
<211> LENGTH: 462
<212> TYPE: DNA
<213> ORGANISM: Akkermansia muciniphila

<400> SEQUENCE: 21

```
atgttcaaca tcgtgagatt caccaggcgt acctgtccgg cattggccct cacgctggcc     60
cttacttcgt gcgacagcag tacgaatgaa gccctgacct ccttcctgac ggggaattca    120
tcccaggaac accagcagct ccaggcccag ctccagcaaa tgaaaaacgc actggcccag    180
acggaacagg aaataagcca ggcggaatcc cacgatgccc gcgttaatta caatcttcag    240
aaaaggcttt ccaacccggg aagaatcacg acgcccttca cggtgaagga tatagatgtc    300
ctgccttcca aacgccgcga cttcgagcac ctgtgctttg acattgaaga catgcgcaaa    360
acgctggcgc agcgcaagca ggaattccat gccctgcaat atcaatataa cgcgtatgcg    420
gccaaactgg ctgaattcaa acaaacccac ccggtagact aa                       462
```

<210> SEQ ID NO 22
<211> LENGTH: 1383
<212> TYPE: DNA
<213> ORGANISM: Akkermansia muciniphila

<400> SEQUENCE: 22

```
atgattgaaa cgattacaga agaacagttg actccccagc aggccgaatt ttgggtgcgc     60
gcccgccagg cggtggacat gaacaattat ccctatgccg tcagcctgct caaggccctg    120
gtaaagcagc tccccggttt tctggaaggc cgcaaggcgt tgcgcgcctg tgaaatcaaa    180
ttgaatccgg aggccaagag aggggggctg ttcagcggta tgaaaatcag caccagcaag    240
ctcacttctt ccaagaagga cgcggctacc cagctttccg ctctggaaga cgaattggaa    300
aatgatcctt acagcattcc ggtaaacgag gccctgtaca cggctgccat ggaagtaaat    360
ttcccggatc tggccgcttt tgctctggag accgttcgcc aggggcatcc cggcaacaag    420
aaaatgctcc acatgctggc ctcccattac gtttcccggg atatgccggc ccaggctgcg    480
gaagtgtacc atgaccttgt gaagctggat cccacggaca gtgtggccgt aaagagcgaa    540
aaggactgca tggcgcgcgc cacgatgcag cagcagaagt gggaggaggc taaaagcttc    600
cgggacgtga tgaagaactc gtcggaaacg aacacccctgg acaagagcga caagaaaggg    660
ctcacccgtg cggaactgga agagcgcctg gggcttctct ccgcccgtta cgcccagaac    720
cagcaggatc tggccgtcgt gcgcgacatt gccggcgttt atgaacaaat ggaagattgg    780
gccaatgcct attccttcta taattacgcg ttcagcctca gcaacaatga tatttccctg    840
gaaaacaagg cctcggaaat gaatgagcga tgccgcaagg cccaggtgga ggaaatccgc    900
cgccgcgctg ccgcggagcc ggataataag gaacttcagg aacagcttgc ccagttcagc    960
aaggaagctg cggagcagca ggtggccttg tgccgccagc gtgtggaaaa caaccccacg   1020
gacccgcaaa cccgttttga gctgggccag gccctcttcg actgcggcaa ttacacggaa   1080
gccattccgg aactccagcg cgcccgcaac aatcccccata tccgcatccg cgccatgctg   1140
ttgctcggca agtgctatga cgccaagaac atgcatgata tggctctgcg ccagctggag   1200
```

| | |
|---|---|
| gaagccaata aggaattgat agaaatgaat gacaccaaga aggaaatcct ttacatgatc | 1260 |
| ggcttgcttt gtgaaaagca gggcaagaag ggggaatccc tggctgcatt ccagcagatt | 1320 |
| tacgacgccg agtacggcta ccgcgacgta gccaggcgcg tggaatcctc ttacggcaat | 1380 |
| tag | 1383 |

<210> SEQ ID NO 23
<211> LENGTH: 468
<212> TYPE: DNA
<213> ORGANISM: Akkermansia muciniphila

<400> SEQUENCE: 23

| | |
|---|---|
| atggaaaata catatcgtca tgcccagctt ccggaagggc gcgttcccgc cctgcgcgtg | 60 |
| gaaccaatgc ctgcggatac caatcagagc ggggaagtat tcggcggctg ggtgatgagc | 120 |
| caggtggacc ttgcaggagc caataccgcc atgcgctatg cattgagccg ctatattgtg | 180 |
| acgcgtgcgg tgagcagcct gacgtttgaa gctcctgtgc tggtgggcga tgtagtgtcc | 240 |
| ttttatacgg atattatcaa ggtgggccgc acctccgtca ccgtgaaggt ggaggtgtat | 300 |
| gcggaacgtc tgacgaagct ttgcaataac attgccaaaa ttacagaggc ggagctggtt | 360 |
| tatgtagccc tgggggagga taagaaaccg attaccctgg aagagtcccg cgcccggttt | 420 |
| gcgcagtgct gttctcttga gacgggagat tcctcttcct gttcctga | 468 |

<210> SEQ ID NO 24
<211> LENGTH: 1413
<212> TYPE: DNA
<213> ORGANISM: Akkermansia muciniphila

<400> SEQUENCE: 24

| | |
|---|---|
| atggggaaaa cgcttttcca aaaatctggg gacgctcata ccgtcggcat cctgccggat | 60 |
| gggagaacgc aaatgttcat cgctacgcac ctgctgcatg aagtcacctc tccgcaggct | 120 |
| ttcggaatgg tccgggacct gggcctgact gtgcgccacc cggaacgcac ctttgccact | 180 |
| gtggaccaca tcattcccac agacaaccag gcggaaccgt tcgcggacgc cacggctgac | 240 |
| gccatgatca gggaactgcg ccggaactgc gctgaaaacg gcatccgctt tttcgacctc | 300 |
| cctaccgggc tccagggcat cgtgcatatg gtagggccgg aactcggcat cactcagccg | 360 |
| ggcatgacta tcgtatgcgg agactcccat acggccaccc acggagcctt cggtgccatt | 420 |
| gccatgggca tcggcaccac gcaggtgcgc gatgtgctgg ctacgcagac cctggccctc | 480 |
| agcccgctca aggtgcgccg catcaatgtg aacggaaagc tggccccggg cgtgcgcgcc | 540 |
| aaggatgtag ccctgcacat catcggcctt ctgggagcca agggcggcct gggcttcgcc | 600 |
| tacgaatacg gaggcgaggt cattgacgcc atgagcatgg acgaacgcat gaccctctgc | 660 |
| aacatgtcca ttgaaggcgc ggcgcgctgc ggttacgtga accctgaccg gaccacggtg | 720 |
| gaatacatca aggacgcct gttcgccccc accggcgcgg actgggacaa ggccgtggaa | 780 |
| cgctggctgg gctttgcttc cgacgcagat gcggaatatg atgaaatcgt ggaaattgac | 840 |
| ggagcttcca ttgagcctac attgacatgg gcatttctc cggaccagaa tacgggcatc | 900 |
| agcggcagca ctcccaaccc atccgacgca cggacgacg atgaacggaa gatgatcaat | 960 |
| gaagcgctgg aatacatgaa attccccgcg gacatgcctc ttaaggggct gccggttcaa | 1020 |
| gtgtgcttcg taggttcctg caccaatggg cgcatttcag acttccggga agtggccgcc | 1080 |
| ctcatcaagg gtcgccatgt ggccccccggc atcagggcgc tggccgttcc cggctcccag | 1140 |
| atgactgccc ggcagtgtga agaggaaggc atcgcggaca ttttccgtga agccggcttt | 1200 |

-continued

```
gaatggcgtc tggcggttg ctccatgtgc ctggccatga atccggacaa gctccagggt    1260
gaccagctct gcgccagttc ctccaaccgg aacttcaagg gccggcaggg aagccccacc    1320
ggacgcaccc tgctgatgag cccggccatg gtggccgccg ctgctctgac cgggaaagtc    1380
tccgatgccc gcgaagtgtt ctccctgaat taa                                 1413

<210> SEQ ID NO 25
<211> LENGTH: 1785
<212> TYPE: DNA
<213> ORGANISM: Akkermansia muciniphila

<400> SEQUENCE: 25
ttatttgtta aagttcacgg gaatgggcgt ttttaacgga agcaccagct tgaagggtac      60
aaaggcccct gccgccgcgt ccaccttggc gtccttggct cccagttcca tgatctggcg     120
ggcttccagt ttgacgtctc cgggcttgaa agtgaacagg gattccttgt tccgtctat     180 ttttgcctgg aggtcctgga tgattctctg gccgccagg ctgcgccgga cgaatccggt     240
caggcggatg gcgttgacgc tgtaaacgcc cgcttcatcc tcgctggatg cgttggcgga    300
ggcctccgtc ctgatgtcat ccaccaggga tgtattttg tccgatgtga aggaatcctt    360
gatgacggaa tatcccgtaa tttgggtggt atcctccgga ttgaagtggg ccagcggttc    420
aaaatccgta aaccagtagg gataatcctt gtgttccgac tgttccagca ggtgcctgat    480
gatgtccgcg tagccgtagc gctgaagcgt gagctgctgg taggaagcca gggtggagtc    540
cagttttttc agctcctgtt ctttctggcg cagggcggat tgtgccgatt tgatggaagt    600
aacggtgggc tggacgccgg cgaggatttc ctccgccttt ttctcgccca tatatcctgt    660
gacggcataa gctgcggcac caagaacggc aatggctgcc ccggcgatga tggcgggcat    720
ttttttctgg ttggcccgct ttttggcaac tgcggtgggt tccaggtcaa tattgaggga    780
ggccctgccg atggagtgaa tggcggtgcc gatcaatccg cccaggatga aggcttcgcg    840
ggagatggtg ttcacgtcca cgccggagcc cacgcccacg ttgtgcatgg ggttgaagaa    900
ggagatcgga atgcccagtt tatcttccag gaattccttg gtatagggca gggaagctcc    960
gccgccgcac aggtatgcct tgacgggagc gcttccgctc atctgggcgc ggtaatggtt   1020
ggtggtccgc tggatttctg aggcaagcct ggtcatggcc gtacggatga cggtagccag   1080
attggccgtg gcgggatcca gcccttccgt ttgcccgttg ctcatggaaa cgagcccgct   1140
ggtggttttc aagcgttccg cttccaggaa gggaatattg aattcacggg cgatagcgga   1200
ggttacgaag attccccccg cggaaatgct gcgggtgaag aaacgtccct gttcgctgta    1260
aatcaaatcc gtggatttgg cgccgatgtc gatgagcatg accggttctt tctcatccgg    1320
ataactgtcc acatacgcat tgtacagaga ggtaagcgcg cagtccactt tgccggtgga    1380
aaggccgtgg agacgattt catcattcag ggagtccagg tcttccgcct tgatggcaac    1440
caggatggct tccgttcca gacctttggc gggaagcaga tggtagtccc acacgacttc    1500
gtccagcggg aaggggacgt gctgctgggc ttcaaagcgg atgagctgtt ccacatcggt    1560
atcgtccaga gccggaagct tgacgaagcg gatgaaaacg gattgtccgg aaacggaata    1620
gttgacgacg cttcctttga cgttgagttc ctggacgagg tcggcgatgg cttcccctat    1680
tttcgtcagg cgcaaacctt ctgctgacgg gtccagcact acgaggcgcg tagcatagcg    1740
gtccaggata agggcgtctt tggaagtctt ggaaaagacg cccat                    1785

<210> SEQ ID NO 26
```

<211> LENGTH: 2961
<212> TYPE: DNA
<213> ORGANISM: Akkermansia muciniphila

<400> SEQUENCE: 26

```
atgttcacca atattacacg cacgaccctc tgcattactg cgttcagcat cgccagcctc      60
atggcggcgc ctctgaatgc aaccaaaacg agagagcctgg attggaactg gaaattcgcc     120
cgtttcggga aaatgccgga tggcagtacg caaccggaac cgggaaaagc catgggattc     180
gccactgcca ccagtgaaga atccggcaat ccggcggaca atgccgtgga cggggacaag     240
tccacccgct ggtgtgccgc cagtggcaaa agcggagaaa aaatcaccgt ggacatggga     300
cgccccgtag atgtaaaaac cgttaacatc ctgtgggaaa acaaagcaa ccatctttc       360
aagctggaag gctccggtga cggaaaacgc tgggcaacta ttgaagacaa aacttccggg     420
caaaacgact ccaaggaaga cacggtagaa acaaaaccg gcaaaccgcg atacttccgc      480
atcaccgtca cgggcaacaa ccagagcaac tgggccagca tccgtgaaat cacctttaaa     540
aacgacaagg gggaaattat ccgccctcag gccgccgccg aaccagtaa ggcggacaat      600
ccctccagcc cctctttcaa cgacaaaaac tggcgttcct tgaacctgcc gcacgactgg     660
ggcgtggaag gaccctccg gatggaaatt gaaaacagaa ccggaaaact cccctgggtc     720
ggcattggct ggtaccgcaa aacgctggaa atcccggcgg acgccaaggg caaccaattc     780
tatctggact ttgacggcgt tatgtcccgc cccaaaattt atgtgaacgg acacctggcc     840
ggcgaatgga atacggtta cagctccttc cgcgtggaca tcacgcccctt cctgaaattc      900
gggcagcaaa ataccattgc cgtcagagtg acaatcccc ccagcacctc ccgatggtat      960
ccgggcggcg gcatctaccg ccatgtgtgg ctcacggaat ccaaccctgt gcacatcgaa    1020
cactggggcg ttttcgtcaa aactccggaa atcaccaat ccgccgccaa ggtagaagtg     1080
gacaccacgg tgaaaaacac cacggacaaa gccgtcatcc ccactgttac tgaagaaatc    1140
ctggacggag gtaaaatcgt agcctccaca accaccaaag gggaagaaat tcccgccggg    1200
gaaaagggca aaatcaccag tacgctgacg ctcaaaaacc ccactctgtg gacgctaaac    1260
gctccccatc tgtataagat gaaaaccacg gtcaggatgg gagacaaagt catagaccaa    1320
aaattcacca acttcggcgt aagaaccgtt gaatggaaac ccacgggatt ctaccttaac    1380
ggggagcgcg tgcagctcaa gggcgtttgc cagcaccatg acctgggacc gctcggctcc    1440
gccgcccaca cgcgaggcta tgaacgccag attgaaatcc tgaaggaatt cggcgtcaac    1500
tccatccgca cgtcccacaa cccgcctgcg ccggaagtgc tggacctgtg cgataaaatg    1560
ggcatcctgg tcattgacga acttttcgac gtatggcaat gctccaaaga aggcgtcaac    1620
aacgaatcct ttaacgaatg gcatgaacgg gacgtggtta acctctgcca ccgggaccga    1680
aaccaccccct gtgtcattgc atggagttcg ggaaatgaag ttccggaaca gggaatgaaa    1740
aatctgcacc atatctccca aaccctgacg gatcttttcc accgggaaga ccccacgcgt    1800
aaagtgactt ccggctgcaa caacgccaat gccgcacgca acggctttgg ggacaccctg    1860
gatgtttacg gctataacta caagccctgg gcctacaagg acttcgccaa ggaccgcccc    1920
caccagccgt tctatggtgc ggaaaccgcc tcctgtgtca gctcccgcgg agaatacttc    1980
ttccccgtgg actggaacaa aggcaaggga ttctacctct accaggtcag ttcctatgac    2040
ctgtacgccc ccggctgggc caaccgtccg gatgtggaat tcgccgctca ggaagacaat    2100
cccaacagcg cgggagaata tgtatggacg ggctttgact acattgggga acccaccccg    2160
tacaatctgg acgccaccaa cgccctgaac gtgccggaag ggccggaacg cgaaaagctg    2220
```

| | |
|---|---|
| atggcggaac tcaaaaaact gggagaccgc gcccctccc gcagctccta cttcggcatc | 2280 |
| gtggacctgt gcggcttcaa aaaggaccgc ttctacatct accaggccca ctggaggccg | 2340 |
| gatctcaaga tggcgcacat cctgccgcac tggaactggc cggaacgcaa ggggcaggta | 2400 |
| acgcccgtgc atgtctacac cagcggggat gaagcggaac tcttcctgaa tgggaaatcc | 2460 |
| cagggcgtcc gcaaaaaggg caccggggaa aaggaccgct accgcctcgt gtgggaagac | 2520 |
| gttaaataca cgcccggcac cctcaaagta gtcgccaaaa aggacggtaa aatctgggct | 2580 |
| acggacacgg taaccactac cggaaaacct gcggcgctca ccctcaagcc ggaccgcaat | 2640 |
| gaaatcaagg gagacggcta tgacctgtct tatgtcaccg tagccgtccg cgacgcccag | 2700 |
| ggccgtatgg tgccccgaag caaaaaccag ctcaccttca aggtaagcgg ccccgcggac | 2760 |
| atcgccggca tctgcaacgg tgatcccacg gacttcacca ccatggcgaa tccggaaaac | 2820 |
| aagaaaatca tgaaaatcaa ggccttcaat ggtcttgccc aggtcattct gcgctcccgc | 2880 |
| aagggagaat ccggaaaagt gacgctccaa gtcatctcca acggactcaa gccggctcag | 2940 |
| acaactgtga cggtcaaata a | 2961 |

<210> SEQ ID NO 27
<211> LENGTH: 1161
<212> TYPE: DNA
<213> ORGANISM: Akkermansia muciniphila

<400> SEQUENCE: 27

| | |
|---|---|
| atgaatgaga aatcgttgat tccgtctatc cgctttgccg gatttactga cgcatgggaa | 60 |
| cggcgtaagc tggggggattt agcggagttt agaagagggc taacctattc accaagagat | 120 |
| atatcaacat ctggaatcag ggtattgcgc tcgtcaaata tagatgagga ttctttcgtt | 180 |
| ttagcagagg atgatgttta tgtaaaagag acggctgtgt gcatcccgct tgttgaaaaa | 240 |
| ggcgacattt taattaccgc agctaatggc tcaagcagat tagtcggaaa gcatgctttg | 300 |
| attattgacg ataagggtaa aatggtacac ggcgggttca tgctgctcgc gcatccgtat | 360 |
| acgcattctg ctttcgttaa tgctcttatg catgcaccct ggtactcatc gtttatccgc | 420 |
| actaacgttg ctggaggaaa tggagctata ggaaatctga ataaaagcga tttggaagaa | 480 |
| caagatattg cggcgacctc tgagcaagag caagaaagaa tcggttcctt gtttgcctcc | 540 |
| ctcgaccatc tcatcaccct tcatcagcgt aagtatgaaa agctccttaa catcaaaaaa | 600 |
| tcgatgttgg acaaaatgtt cccgaaaaat ggtgagcttt ccccgaagt tcgctttgcc | 660 |
| ggatttactg acgcatggga acggcagaag ctggggggatt tggtagagtc tgttccgttt | 720 |
| aagcagtata tagcatcacc tgaacctgac ggaaaattcg aaattatcca acaaggaagt | 780 |
| gagcctatta ttggatatgg aaacggaatc ccttgtgaag attatgcaaa gataacgatt | 840 |
| ttcggagacc atacagtttc aatctacaaa ccacaaaagc cctttttgt agccactgat | 900 |
| ggcacaagac tccttacagc aagagttcta gatggagatt ttttttatt cctcttggag | 960 |
| cgatacaaac caatccctga aggatataag cggcattaca cgatattgat tgaaaggtat | 1020 |
| ggatgttttc cttcccatcg agagcaaaag ttaattgcca tatttttag gaacatcgac | 1080 |
| cacctcatca cccttcatca gcgtaagttg gaaaaactgc aaaacatcaa gaaagcctgt | 1140 |
| ctggaaaaaa tgtttgttta a | 1161 |

<210> SEQ ID NO 28
<211> LENGTH: 564
<212> TYPE: DNA

<213> ORGANISM: Akkermansia muciniphila

<400> SEQUENCE: 28

| | | | | | |
|---|---|---|---|---|---|
| gtgaaaggat | ttttttgccc | gttttcaacg | ggtttatgga | aggaacatgg | ctggaaatgc | 60 |
| ggaaaagggt | atgttaatga | acagggcatg | gaaagattgt | atcgtccgaa | tgttgcgggg | 120 |
| atgatggtcc | ggcaggacgg | gaaattgttg | atttgcgagc | gttccgggca | gaaaggagcc | 180 |
| tggcagtttc | cccagggcgg | aattgacccg | ggggaaacgg | ctttggaagc | cgtgcggcgc | 240 |
| gagattgggg | aggaagtggg | gttttgccg | tcccagtata | atattgtgga | atcccggaag | 300 |
| gggtatcgtt | acgattatcc | gccggaggtg | ctggagtatg | ttcgtgaaaa | gcggcggcag | 360 |
| cctttgttg | ggcaggcgca | ggagtatttc | ctgtgctggc | tgcatgcgga | cgctccggaa | 420 |
| cccgtcctgg | atgaccggga | gttttgcgat | acaagtgga | tagccccagc | cgaatttaag | 480 |
| ctggagtggc | tgccggagtt | taaaaagaaa | gtttacgcca | gggttctgga | agatttcttt | 540 |
| aatgtccggg | cgcgggataa | gtaa | | | 564 |

<210> SEQ ID NO 29
<211> LENGTH: 1422
<212> TYPE: DNA
<213> ORGANISM: Akkermansia muciniphila

<400> SEQUENCE: 29

| | | | | | |
|---|---|---|---|---|---|
| atgtctattt | tctcatcacg | cagacaattt | ctcaaatctt | tggggcttgc | ggccggagcg | 60 |
| gctgccgccg | gaaatgccct | ccctgggaag | gctgtggaaa | tccctgccgg | agaccatctc | 120 |
| tggaaatccg | cctctccggc | ggctccgagg | ccttccggtt | ccacatacat | gggagggttc | 180 |
| aaggctcccc | ggctgggtcg | catcaggctg | gccttcatcg | gcgtgggagg | gcgcgggttc | 240 |
| tcccacctgg | cgcaaatgtg | cgtgatggat | ggagtgaaa | tcgtgggcat | atgtgatttg | 300 |
| aaggaagagt | tgacgaaacg | cggcgtggat | cgcgtgctct | ccagaatggg | gaaaagccct | 360 |
| ttgggctatt | ccggcggcga | tatggaatac | ctgaccatgc | tgaaggagct | gaagccggat | 420 |
| gccgtcatca | tcagtacgga | ttggagttcg | catgccagaa | tcgcctgcga | cagcatgaag | 480 |
| cacggcgctc | acgcctttgt | ggaagttcct | ctggccgtct | ctctggagga | gctctggagc | 540 |
| ctggtggata | ccagcgaggc | caccaggaaa | cattgcatga | tgatggaaaa | cgtcaactat | 600 |
| gggcgggatg | aactcatgtt | cctgaacatg | gtccggcagg | gcgtcatcgg | cgatttgctt | 660 |
| cacggggagg | ccgcgtatat | ccattgcctg | gtgacgcagc | tggggacac | gcgcggggaa | 720 |
| ggggcctggc | ggccggaata | tcataccaga | atcaatggca | acctgtaccc | cacccacggg | 780 |
| ttggggccgg | tggctcaata | tatgaatttg | gagcgtggag | aggaccgttt | ctgccgtgtg | 840 |
| gcggcgttcg | cttctcctgc | tctcgggcgc | aatgcctacg | ctaaaaagca | tcttcccgcc | 900 |
| gatcaccgct | ggaacaatac | tccattcatc | tgcggtgaca | tgaatacggc | tgttgtcaag | 960 |
| acgcagctgg | ggcggaccat | tcttgtccag | ctggatgaga | cgtccccccg | gccttactcc | 1020 |
| cgcgccaacc | tgatccaggg | aacggagggc | acgctggctg | gtttcccaac | ccgcgtggcg | 1080 |
| ggtgaaaagc | tgggcaacgg | caattatcat | gaatggattg | aaggcaggga | aaaactggcc | 1140 |
| gctatttatg | aaaatacga | tcatccctc | tggaaacgca | tcggggagct | ggccacgaaa | 1200 |
| atgggcggtc | acggcggtat | ggactttgtg | atgctttccc | gcatcgtgga | atgcctccgg | 1260 |
| aacggagaac | caatggatca | gaacgtttac | gaaggagctt | cctggtcttc | cctgctgccg | 1320 |
| ttgacagccc | gttccatcgc | ccagggcggg | atgcctgtgg | aatttccgga | ttttacccgc | 1380 |
| ggagactgga | aaaccaccat | gccgctggcc | gtggtttcat | ga | | 1422 |

<210> SEQ ID NO 30
<211> LENGTH: 816
<212> TYPE: DNA
<213> ORGANISM: Akkermansia muciniphila

<400> SEQUENCE: 30

```
atgaaaactg tcttagtagt tttattgatt cttgcagcag gggcgggcgc ctggttctcc      60
ggtcttagcg gccttttcgg tattaatggc cagtatcagg attttaaaga aatgatttcg     120
tatcgtaaga ctttggacaa ggaaatacgt acttggacaa gcttgcgcaa cgacatgatt     180
aagaatcgtg gcttggcagc ggaagaaaat cttagtctga tttccaacaa ggcttccgtg     240
acgcagcagc gtgatgaaca gctttccaag gaagcggagt tgaaggaaga agaagtgcag     300
ttgaatgcgg acttgtccaa aatcaataaa cagattgagg aattaaagag caagttgcaa     360
gatttcggtg tttccagcgt acaggaaatc caggagaaga tggaatcttt ggaagcttcc     420
aataagaagc tccaggaaga tattgaccag attaaaagtg ctacggaagt ggcttccaag     480
agacgggcag aacaagcttc tgagctggct agccgccaga aggagcaagc tgaataccga     540
gctgctcttg ccaaaaatgg ggaagagtat cccgttctat ccgtggatcc gcagtggggt     600
tttgttgtga ttggggccgg acagggcagt agtattgatc caaatacggt tcttcttgtt     660
acccgtgaag tcgcagcat tggtaaatta aaggtaactt ccctggagaa aaatcagacg     720
gtagctgaca ttattaaaga cagcgtaccg tctggtatga gtattcaacc cggcgataga     780
gtacaactcc tgcgtccccg tcagtccgcc aaataa                               816
```

<210> SEQ ID NO 31
<211> LENGTH: 429
<212> TYPE: DNA
<213> ORGANISM: Akkermansia muciniphila

<400> SEQUENCE: 31

```
atgctggact tgagcgcttc tctttccacg gaagatgggc tagggccgtg gaatattatc      60
gtcaaattga cgggcaatgg ttcggacctt ccccaggtaa gcattaatgc ggcaagcagc     120
aatgaaagtg ctcctatgaa cattgcttcc gtagtgtacc gcaggacggg atcatccgct     180
attctgaggg ggaacttcac gattacttcc gggcagtgga cggctccggg cccgattgtc     240
gtgacaaaca gggacaaggc cttatatgat gctaatattt ccttcagttc ctccaatgaa     300
cgtgagagct gcggcgggac gttcaccggt tccatcactt accaggttcc cgttgagaat     360
gatgaaggcg aggttgaagc gcaggactgg accgctacgg aaggaacggt gagttacacg     420
gtatcctga                                                             429
```

<210> SEQ ID NO 32
<211> LENGTH: 1446
<212> TYPE: DNA
<213> ORGANISM: Akkermansia muciniphila

<400> SEQUENCE: 32

```
atggatagca ttctttccgt ccttgccact atcgccatta ttttcggcgt ggtgatgttg      60
tttaacttca tgatttttat tcatgaactt ggtcattttt tcgctgcccg ctggcgtggt     120
ctgtatgtgg acagatttca aatctggttt ggccgtccca tctggaaaaa aacggttaac     180
ggcgtgcagt gggggctggg gtggattccg gccggaggtt ttgtatccct gccgcagatg     240
gctcctatgg aggccattga aggacgtgcg gagcttccca aggatttgaa gccggttact     300
```

```
cccttggaca agattatcgt ggccgccgct gggcctgccg cttcttttct gctggctgtg      360
ttgtttgccg tggccgtctg gatggtgggc aagccggatg tggagatggg cgtgactacg      420
gtcggttttg ttgctccgga cagccctgcg gctcaggccg cattcttcc cggcgacaag       480 attgtgaaag tggacggcca tcctgtggac aagtgggcgg gcaatatgga aggcgtgcgg      540
gaattgatca tgctgggcga gcatgaccgg gtggttttta cggtgcagag acctggacat      600
gaaggagaga tggaaatttc ctgcggattc cggattccgg aaacgtcctg gtggcagcgc      660
tccggcatgc gtcaggtggg gttgatgcag gccatgccct gcgtgattgg ggaagtgatt      720
cccaattctc ctgccgcact ggccggattg aacccgggcg ataaggttgt gggtgccaat      780
ggagaacgcc tctggaaccc tgccgcactg gatgttctgc tgaagaagaa tgaaccgctc      840
ttgctggatg tgacggacag ggccggggtt gcaaggcagg tgaatatcca ggggaagctt      900
ccggagaatt ggcacaatgg tgcggacggt tccctgctca agggggccca gcctattctg      960
ggcgtgagct gggacctgag ttccgtgggc cgagacgtta ccgtccatcc ttctccgtgg     1020
gcgcagatca agcagagtct gaaatggatg ggggataccc tggcgaaggt ggtggctccc     1080
ggcagcagcg tgggcgtgga gcatctttcc ggacctgtgg gaattgccaa tcagttttac     1140
aagatgttct ctctggagga agggtggaag ctggcccctgt ggttttccgt ggtgttgaac     1200
gtgaacctgg cggttctgaa tattctgcct cttccggtag tggatggcgg ccatgtggtc     1260
atgaatgcca ttgaattggt tttccggcgt cccctgaatg taaaagttct ggaattcgtc     1320
cagttcggct ttgtgttcct gctgatgggg ttcttcctgt ttgtgacatt caaggatgtg     1380
ggggatttct ttggcaagaa gccggacaag ctgcccaccc cggtattcaa ggccgtcgcg     1440
gattag                                                                1446

<210> SEQ ID NO 33
<211> LENGTH: 927
<212> TYPE: DNA
<213> ORGANISM: Akkermansia muciniphila

<400> SEQUENCE: 33
atgaagattc tcgtaaccgg cggcgccgga ttcatcggtt cccacattgt ggaacactat       60
caggataagg cggaggaaat ccgtgtgctg dacaacctgc gcacgggcta tctcaagaac      120
ctggaagggc tcaggcacac gttcatcgaa ggttccatct gcgaccggga gctggtgcgc      180
caggcggtgc agggagtgga ctatattttc cacatggccg cgctcgtctc cgtgccggaa      240
tccatgagca gatcagcga atgcatcgac atcaacgtca acggtttgct gaacgtgctg      300
gaggaagctt ccgccgccgg agtcaaaaaa atcgtgctgg cgtcttccgc cgccatttac      360
ggagacaatc ccacggtgcc caaactggaa accatgtacc cggaacccaa gagtccctat      420
gccattacca agctggatgg ggaatactac ctcaacatgt tccgggcgga aggaaaaatt      480
aatacggcag ccgtgcgctt cttcaatgtc ttcggccccc ggcaggaccc caagggcgcc      540
tatgccgcag ccgtgcccat tttcattgaa aaagctgtca aaggagaaga catcaccgtg      600
tatggggacg gctcccagac gcgcgatttc atttatgtga agacattgt aggagccctc      660 acctttgtgg cggaacaccc ggaagtcacc ggcgtgttca atgccggtta cggcggccag      720
atcaccattg aagagctggc gcagaacatc atcaaggctg ccgggtcttc ctccaaggtg      780
cttcatgccc cggaacgtcc gggagacgtc aagcattccc gcgcctgtgc ggacaagctc      840
cgcaatgccg gatggcagcc caggcatact ttgccggaag gcctggcgac gacgctggaa      900
tacttcaagg gcattctggg caggtaa                                          927
```

<210> SEQ ID NO 34
<211> LENGTH: 1200
<212> TYPE: DNA
<213> ORGANISM: Akkermansia muciniphila

<400> SEQUENCE: 34

```
atgtataccc ccgaattcaa aaacatcctc acttccaccc tggacggact gcgtgcggaa        60
ggactttaca aggaagaacg ctttatcgcc tcccagcagt actcccaggt gacgctgaag       120
gacggacgct ccgtcatcaa catgtgcgcc aataattatc tgggccttgc taataatccg       180
gaagtgatgg aagccgccaa gaaagccatc gaccagtggg gtttcggcat ggcgtccgtg       240
cgttttatct gcggcacgca gacccttcac cgtcaattgg aagaacgtct tacccaattt       300
ctcggcacgg aagacacgat tctgttccc tcctgctttg acgccaacgg cgggctgttt       360
gaaggcctcc tgactgcaga cgacgctatt atttccgatt ccctgaacca cgcttccatt       420
attgacggcg tgcgcctctg caaagccaag cgcttccgtt atgccaacaa cgacatggca       480
gacctggaag ccaagctcca ggaagcggac gccgccggag cgcgcgtgaa gttgatttcc       540
acggacggcg tcttttccat ggacggcatc attgctcagc tggacaagat tcacgagctg       600
gcagccaagt acaatgccat tgtccacttt gacgactgcc acgccacggg cttcctgggc       660
gaaaagggcc gcggcacgca tgaataccgc ggcctgttcg gccatataga catcaccacc       720
ggcaccctgg gcaaggcact gggaggcgct tccggcggct acgtctccgg cccgaaagaa       780
gtagtggatg tcctgcgcca gaaggcgcgc ccgtacctgt tctccaacag cgtggccccg       840
gctatcgtag ccgcttccat caaagtactg gacctgttgg aacagtccac ggaagcgcgc       900
gaccgcgtag aagccaatac caagtatttc cgtgacgcga tgacgggagc cggattcacc       960
atcggcggca aggaccaccc catttccccg gtcatgctgg gggatgccgt cctgtcccag      1020
aaattctccg cccagcttct ggacgaagga gtgtacgccg tcggcttctt ctatcccgtc      1080
gttcccaagg gacaggcccg catccgcacg cagatttccg cagcccatac ccgcgaacag      1140
ctggacaagg cgattgaggc cttctgcaag gtaggtaaaa acctgggcgt tatttcctga      1200
```

<210> SEQ ID NO 35
<211> LENGTH: 2745
<212> TYPE: DNA
<213> ORGANISM: Akkermansia muciniphila

<400> SEQUENCE: 35

```
atgtccacca ttcctgcgc gtgtagcgca tctactgaca aattcgtcta ttctttcggc        60
ggagggtccg ccgacggcaa tggcagcatg aaaaatcttt tgggcggcaa gggcgccaac       120
cttgcggaaa tggcccgtat cggccttcct gtccctcccg gattcaccat cactacggaa       180
gtttgcactt actactacga tcacggctgc acttatcccg cccagcttga cgcgcaggtc       240
aaggaaggca ttgccaaaat ggaacagatc ctggacgca gttcggcga tacgaagct         300
atgcccctgc tggtggccgt gcgttccggc gcccgtgaat ccatgcccgg catgatggac       360
acgattttga acctcggcct gaatgaaaaa tccgtggaag ccatggtgaa ggctacgaac       420
aaccccgct tcgcctggga ctgctaccgc cgcttcgtgc agatgtacgg cgacgtggtg       480
ctgggtgtgc agaaaaaccc ggatgaagac cacgaaccct tgaaaccgc atcgctgcc         540
atcaagaaag aacgctttgg cagcgaggac gtggaagaca ccaagctctc tgccgatgac       600
ctgaaggaac ttgtctcccg cttcaaggcc ctggtgctgg aacgcaccgg ccatgaattc       660
```

```
ccggaatgcc cctgggaaca gcttcaggga gccattggcg ccgtgttcgg ttcctggaac      720
aatgaccgcg ccatcgtgta ccgccagaaa tacggcattc cgtccgaatg gggcaccgcc      780
gtcaacgtgc aggccatggt cttcggcaac acgggtgagg aatccggttc cggcgtggcg      840
ttcacccgca accccgcctc cggcgaaaac gaattctatg cgaattcct gatgaacgcc       900
cagggtgaag acgtcgtggc cggcgtgcgt acgcccgccc ccgttgctgc ccttcatgaa      960
gtgatgcccg ccgccttcaa tgaactggtg cgcattcgcg aagtgctgga aaaccacttc     1020
catgacatgc aggactttga attcaccatt caggaccgca ccgtctacat gctccagacc     1080
cgcaacggaa agcgcaccgg cgtggccgct ttccgcattg cctgtgaaat ggtgaacag      1140
ggcctgattg actggaaaac cgccgtgcgc cgcattcctg cggaccaggt ggaccagctg     1200
ctgaccccca tctttgaccg tgaagccatc aagagtgcca aggttctgac ccgcggtctt     1260
cccgccgggc ccggcgccgc caccggacgc atctacctga acgcggaacg ctgtgtggaa     1320
gccgcggata gaggtgaaaa ggttctgctg gtccgtctgg aaacctctcc ggaagacctg     1380
cgcggcatga ttgccgctga aggcatcctg accgcccgcg gcggcgtttc ctcccatgcc     1440
gccctcgttg cccgccagat gggcaaagtc tgcgtttgcg gcgcggatga aatcattgtg     1500
gactacaaca accgcaccgt ttccgttggc gacgtaacca tcagcgaagg tgactacctc     1560
tccattgacg gaacgagcgg cctggtatac gccggcaagg tggaaacttc cccctctgaa     1620
atcatccagg tcctgatttc caagaccatg aagccggaag acagccgcac ctaccagaac     1680
ttcgccaagc tcatgcagtg gtgcgacgac tgtaccaaaa tgaaagtgcg caccaatgcg     1740
gactctccca gcagacggaa aaccgccatc gccttcggcg ccaccggcat cggcctctgc     1800
cgcacggaac acatgttctt tgaaggggac cggatcgact tcgtccgtga aatgatcctc     1860
tccaccaaga gagcgaccg cgtagccgcc gtttccaagc tccttcccta ccagaagggg     1920
gacttcaagg gcatcttcaa ggcgctcaag ggcctgccgg gcaccatccg ccttctggac     1980
ccgcccctgc acgaattcct tccccagacg aaggaacagc agcttgacct ggcccagaaa     2040
atcggcatgc ctgtggaagt tatcatgcgc cgcgtgtccg aactccatga gttcaacccg     2100
atgctcggcc accgcggctg ccgtctcggc atcgcctatc cggaaatcac ggaaatgcag     2160
gcccgcgcca tctttgaagc cgctgtggaa gtctcccagg aagaaggatt tgccgtggtg     2220
cctgaaatca tggttcctct ggtggccttc aagaaggaac tggacatcca gaaagccatc     2280
attgacaagg tgcccagca ggtatttgag gaaaaaggcg tcaaagtgga ctacctcgtc     2340
ggcaccatga ttgaaatccc gcgcgctgcc gtcacggctg acgaaatcgc ggaaaccgcc     2400
cagttcttct ccttcggcac caatgacctg acccagacgg gcctgggcat gagccgcgac     2460
gactccggct ccttcctgcc gcagtaccag gaactggaaa tcatcaagaa gaacgtcttc     2520
gcttccattg accagaacgg cgtcggcaag ctgatgaaga ttgccgtgga actcggccgc     2580
tccacccgcc cggacatcaa actgggcatc tgcggcgaac acggcggcga ccccgcttcc     2640
gtcaagttct gcaacacgct gggcctgact tatgtgagct gctcgcccta ccgcgtcccg     2700
accgcccgtc tggccgcggc ccaggctgct ctggaacagg aataa                    2745
```

<210> SEQ ID NO 36
<211> LENGTH: 885
<212> TYPE: DNA
<213> ORGANISM: Akkermansia muciniphila

<400> SEQUENCE: 36

```
atgcgtcttt tatcctccgc cgccgtcatt tgcgccgccc tgttctccgg aaccatcctt        60
```

```
catgcgcagg acccggaact gctggccaag cgccagtgcc gttccgtcca tatcaaccag    120
caggggcatc cctcccaggc aagcgccctg tacaatgtag tgaaagccaa acatccgtt     180 cccggcacct acttttgcgc catgaatttt gacgacggct atatcggttt tcaggaacaa    240
tccaacggta aaaagtaat catctttcc atctgggatc cggtggcaca cggagacaac     300
cccaatgatg tgccggaaga agaacgcacc aagctggtaa aactgggcaa agatgcgcgc    360 tccgacgtt ttggcggtga aggaacaggc ggacaaagct tcgtgacta tccctgggca    420 atcggggaga acatgcgctt cctcgtctgc gtcaaaaaaa tggggaaatt caaggaaatc    480
agcggttatt actttaataa taaaagcagg tcctgggatc ttatttccaa atggaaaacg    540
cattcctcgg aaaaggaact ttccttctcc gtcggattcg tggaagattt catgcgtaat    600
tttgaatcag ccaagaaggc ccgcggagcc ttctttggcc ccagcttcgc gtacaaggac    660
ggcaaatggc atcccaatac cagcgtaacg ttcaccggcg acccaacccc ctccaccaac    720
gtcatggcga acatccagcc tgatggttcc gtgctgcttc agacggggg aactacgaaa    780 atgacggatt tcaagctgtt ccaaaatcgt cccctgcccc agaatatcaa gctggtcctg    840
cctgacaagg ccgttaccag tcttgttcag gagaacatta actga                   885
```

<210> SEQ ID NO 37
<211> LENGTH: 870
<212> TYPE: DNA
<213> ORGANISM: Akkermansia muciniphila

<400> SEQUENCE: 37

```
atgatagata agacgacatc ccgcgtcatt atggggcttt tgggaacagc ctgtgtcttg     60
attacggcat ttgcctggta caagacgaaa tatgccgccg ttccggaggc cgggatgcac    120
cataatattt atgacgaaga cattccgcgg tctgctccgg ttcctgtaga ttaccggatg    180
gttttgttga cgccccagga gctgcaaag gcgcctctgg ccgatgtgtt tacatcgccc    240
ctcggagatg agaatggagc gtttacctat gttgcccagg gtgtggggga tatgaatgcc    300
gcccgtaagg gaaggcatgc aggacaggat ttaaatggaa taggaggaga aaacacggat    360
gagggactgc ccgtgcgggc cgccggccgc ggattgctga tttatgcagg agaaccttct    420
ccagattggg gcaatgttgt cgtgctgctg caccgcttgc cggacgggcg ttttgtgcag    480
agtctgtatg cccatttgaa aaccgtcagc gatattccgc tggggactct ggtgggacgc    540
ggagagcaaa tcggctcagt cggaactgcg cacggcaatt atttggcgca tttgcatttt    600
gagatgattg aatccatcgc tcatgaggcg ggaatgccgg gctatgggaa gacaacgttt    660
aacagaatca atccggatga ggtgctaaag caatatgctc ccgacccgga aatgatgatg    720
cctgatccta ttattgcctt gaaacaggtt cagatgcgg cggggtggga aaaactgctg    780
gagaatctgt ataaggataa cagcatggaa gctttggata aaatcctccc agacagtcag    840
ccgcccacgg aagaaaagga aaaacgctga                                     870
```

<210> SEQ ID NO 38
<211> LENGTH: 2619
<212> TYPE: DNA
<213> ORGANISM: Akkermansia muciniphila

<400> SEQUENCE: 38

```
atgcccggcg gcaacctgcc gacgctgccc gtcaagcggg tggtgcgtcc cactccctcc     60
attccggacc atgaagttgt acgccagata gggagcggcg cgtacggaga agtatggctg    120
```

-continued

```
gcaaaatccc tgaccggggc gtggcgcgcc gtcaaaatcg tatggaggga ggattttgaa      180
gacgagcgct ctttcaaccg ggaatttgag ggcattctcc agtatgaacc catcgcccgc      240
aaccatccgg ggctggtcca tatcctgcat gtagggaggc atgaccagga ttccccgttt      300
tattattacg tcatggaact gggcgacgac gcccgcaccg gagttcatat tacaccggac      360
gaatatattc cgcgcacgct ccagacggac aagaagtttt ccggcaacaa gcctcttccc      420
ctggattact gcctggaggt aggcagccag ctggcccacg ccctgctgta cctgcacagc      480
aagaacctga cgcaccggga catcaagccg gcgaacgtca tctttgtcaa cgggcgcccc      540
aaactggcgg acataggcct ggtggcccat ctggaccagc gcagctttgt agggacggag      600
ggattcatcc ccccgacgg ccccggcacc cggcgggcgg acgtttacgc gctggccaag      660
gttctgtatg aaatcagcac gggaaaggac cgcatggatt ttcccgaact cccggatgac      720
ttgccggaag gcaccgtgcg caagaaatgg caggccttca acaccatcat ttgccaggcg      780
gcggaacccc gcattgaaga atgctccatt gattccgcag aggagctggc ggaaaaaata      840
gacgccctcc gggggtatga agtgccttcc cgtttccgtc ttcagaagaa aaagaaacgc      900
cgcaaactca cgggccct ccaacttctg gctgcagccg ccgccggagc cctgactgcc      960
tactgggggg ctttatggct caacaacagc cagcatccgc cggaggaacc tgcctcggat     1020
attcatccgg atatccactc atccgctccg gaagaagaat cccggaccgg atacgtgctg     1080
gtgaccagct ccccggcggg agcgtccgtg tatgatgcgg acggcaacta tctggatgaa     1140
actccctacg gccccattga actgccttcc ggctcccggg tagcctatac catcaagaaa     1200
tcggggtttg cggacaagga agaggcggga accgtcaaag gagggtccac gctggccctg     1260
ggcggcgtgc tgaaagagta ccatcccct acggacagcc agccctggaa ggatacggag     1320
ggtgttacgt acctgcccgc agaaacgcgc catgtgcgc aaggccccct taccgccgcc     1380
ctgttcaaca aatttctgaa ggaggaccgc cagaaaggga acttccagat gaaaagggaa     1440
cagacggaac cggggcatcc ggagaaggat gtggccctgc tcacgcagga cggcatcacg     1500
gcctacctgg cgtggctgaa caagaaatgc gagcgggagg ggctgctggg caaggaattt     1560
tccatcaatg cggatccgct tccgcaggct tccggcagca cggaaaaacca caatgcctac     1620 gtcctgaacg tcaccgcgt gttccaggtg cccattaccg tcaccaccaa tccgccggga     1680
gccagcgttt ttttcaataa caggctcatc gggcgtaccc ccattgaaga atacgtcaac     1740
caggttccct acgtcattga aatcaaactg ccggggcacg ccaccatgcg tcgcaggggg     1800
ctggatccgc aggacttata cctttccctg cagttggaac cggacaagtc tgtcgttttt     1860
ggctcgccct ggaccaacag cctgggcatc aaactggtcc ctgtgggtgg gaatgctctg     1920
gtcatgaccc acgaagtgcg cgtaaaggac tttcaggaat tcctgaaagc taccggaagg     1980
aaagctccgg cccggcccgg ctttccccag ggagaagacc acccggtggt gaatgtcagc     2040
aggcaggatg cgcgcgcctt cgccagatgg cttaccagca agagcgggc cctgggcctg     2100 attgatcagc acgactccta ccgtcttccc aaggatgagg aatggagttc ctgggtgcgt     2160
ctgacggatg aacagggagc ctcccctat gaaaagacgc tgcctcatga aaactcccgg     2220
gaagccttcc cgtgggggta ttcatggccg ccgcctgata aacgggaaa ttttgcggac     2280 cagtccgccc tgatttacct gccgtcctcc cgcgttatcg taggatataa cgacggacag     2340
ccgtatacgg ccccccgtaaa aacctttccg cccaaccacc tgggcctgta cgacctggaa     2400
ggaaacgtca tggaatgggt agacgattcc tacggggggc cggaatccct ccccatccgc     2460
aactacggcg tcgcccgcgg aggcagctac ctgtccttcc gccccaaaca gctcaccact     2520
```

| | | |
|---|---|---|
| tccatccgca ctccoctgcc ggaaaatacg agggataacg cgctgggctt ccgtcttatc | 2580 | |
| ctgtcttccg aacgccccgc cattccaaca gctccctga | 2619 | |

<210> SEQ ID NO 39
<211> LENGTH: 1611
<212> TYPE: DNA
<213> ORGANISM: Akkermansia muciniphila

<400> SEQUENCE: 39

| | |
|---|---|
| atgctgacga tcaaaaatct cacaaaatcc cacgccggac ggaccttgtt cagggaaacg | 60 |
| gaaatgacca ttaactgggg ggaacgggtg gctctggttg ccccaacgg agcaggcaaa | 120 |
| tccaccctgt tccgcatgat tctgggagaa gacacgccgg acgaaggctc catcagcatg | 180 |
| gatgaatacg ccatcgtggg ctatcttccc caggaagcca gcgaaccgaa ggatgaaacc | 240 |
| gtcctggaaa tcgccctggg catcacgccg gaaatggaac aggccatcca ccatccgg | 300 |
| acggcggaaa acgccaacaa aacgatacg ccggaatacg cggaagccat tgacaccttc | 360 |
| aacgccgcca acggttacca gctggagccc aaagccaaga aaattctcaa agggctggcc | 420 |
| tttcgggaaa gcgacttcca ccgccccgcc cgggaaatgt ccggcggctg gattatgcgc | 480 |
| gcgtacctgg ccaagctcct tgtcctggag ccggacctcc tgatgctgga cgaacctact | 540 |
| aaccacctgg acctcctgtc cctgctgtgg ctccagcgat acctgaaaaa ctaccccgga | 600 |
| gccatcctga tgatttccca cgaccgggat ttcatggatg agctggtgga aagcgtgtac | 660 |
| gacatcgaca cgaagaact ggtggaatac cgcggcaatt actcggactt cctccaacaa | 720 |
| aaggacgtgc gcttcgagca gcttcaggcg gcctaccgca accagcagaa ggaaatagcg | 780 |
| cacattcagg aatttattga ccgtttccgc tccatcaatt ccaaagccgg gcaagtccag | 840 |
| agccgcatca agcagctgga aaagatgaaa atcattcaaa aaccggtagc ctgcaggaaa | 900 |
| gtatttaaat tcaacttccc ccagcctccg cgcagcaccc agaaagtcat tgagctggaa | 960 |
| aaagtctgcc aatcctatgg cgaccgcagg gtttatgaaa atttggaccct gctggtggaa | 1020 |
| cgcggggagc gcactgttct tgtaggcccg aacggcgcgg gcaaatccac tcttctcaaa | 1080 |
| atcctggcgg gcatcatccc cattgactcc ggacaacgca ctcccggtac cacgacgcgc | 1140 |
| atcggctact ctcccaggc gcgaacggaa aacctgaacc cggaaaatac cgtgctggag | 1200 |
| gaaatcatga atgcagcgc tgaaatccgg gaggaagaag cgcgttccat cctgggttcc | 1260 |
| ttcctgttcc ggaggctgga tgtggaaaaa cgcgtcagcg ttctttccgg cggggaaaaa | 1320 |
| tcgcggctca gcctggtcaa attcctggtg gatccgccca acctcctgct gatggacgag | 1380 |
| ccgaccaccc acctggacct tttgtccgta gaagccctgg tgcaggctct gaagcattat | 1440 |
| gaaggaacac tggtcttcat ctcccacgat gtgcacttca tccgttccct ggcacaaaaa | 1500 |
| accctgcatg tgaaccgggg gaccatcacc gcctacgcag gcggatatga ctactatctg | 1560 |
| gaaaagtcag gcattctgga cgatgaaaaa ggcggcatca cggcggaata a | 1611 |

<210> SEQ ID NO 40
<211> LENGTH: 444
<212> TYPE: DNA
<213> ORGANISM: Akkermansia muciniphila

<400> SEQUENCE: 40

| | |
|---|---|
| atgattcaaa cgtatcaagt actccctgtg gtggccatcg tatgctccgc ttccgccttt | 60 |
| gcccagaacg ctgccgatcc cgtgcagatg gtcaagcaga atatcgacct gatttcttcc | 120 |

| | |
|---|---|
| gccaacaagg ttttggacga cgtgaaggac aacgctgcgg ttgaaatcgc cattaagcag | 180 |
| ctcaatgcgt tgacccagca ggccaagcag ctggacaagt ccatggaaaa gatgaggctt | 240 |
| acttccgagc aggctatccg catcaccaaa ttgaacggag acgcccagga caccatcgtg | 300 |
| gatatgctgg aaaattgcga gcgcattcaa aaggacaagc tgatgactcc ggctttgctc | 360 |
| aaggcggtga atgattttgc cgacgccgcc aacatcgacg tggtggaaac gattacgacc | 420 |
| gtggagcaaa ttgtggaaga ttga | 444 |

<210> SEQ ID NO 41
<211> LENGTH: 948
<212> TYPE: DNA
<213> ORGANISM: Akkermansia muciniphila

<400> SEQUENCE: 41

| | |
|---|---|
| atgagcaata tcaacccatt cattctaaca gggatgatgc cgcttttcagc ctcatccatg | 60 |
| aaccgtgtct cctacatgtg cccggtcacc atcagcaatg atgtagtgca gggccagacg | 120 |
| gacattcagg attcccttac cgttgattcc ggcggaaatc tttacatcat caacgctcct | 180 |
| gtttacgtgg gcggccccaa ccagccggac acgggcacc gcaccgccca cctcgtcatc | 240 |
| cggaacggag cgccatgac gctcctgggc aatctgccgg accatatgac cgttttcctg | 300 |
| ggggacaaag ccaacggcag cctggaaatc aacggcggcc gccttctgat gggccagggg | 360 |
| cgcattcagg cgccaggga gcatgaaggc agaatcgcca tgacggacgg ctggctcttc | 420 |
| gcctcggaag tggatctgcc ggcggagggc tcggaactcg tgatcaggca cggcctgatg | 480 |
| cgtatcagaa aactctccgg caatgcatcc acccgcattt acggaggcgt tctgcacgta | 540 |
| aaggaggaag cccgcgccag ccgcatccat ctgatagacg acggcgtgct gctgctgggc | 600 |
| agcgtcacca gccagcctc cgcggacgtc atggccggag cgggcatcaa cttccgcggg | 660 |
| gacggcggag cgctggtaat ccgcatcccc cacccggaaa acgctctgac gcgcacgcgg | 720 |
| gaagcggaac atgtctttga cgaactgctc cggagggga agctctttca tgacagtgaa | 780 |
| cccatgacca gcttccaggg gttccatatg agggagttca cggggcatga cggactggcg | 840 |
| tacgccgcgc tgcgcccctc cgcccagctg aacgcggaac agaatcaggt tacccgcctg | 900 |
| ctccatacgt tcatgtacgg cggcagtgaa aaggacatgc ccatctga | 948 |

<210> SEQ ID NO 42
<211> LENGTH: 522
<212> TYPE: DNA
<213> ORGANISM: Akkermansia muciniphila

<400> SEQUENCE: 42

| | |
|---|---|
| atggataaac aatccacaga tcataaagag gaaactctgg tggccatgct ggcatctttc | 60 |
| cgcaaggaag cctgttacca tgacaccttc gaggaagatt tcctccgcaa tttttcatctc | 120 |
| agaaaggaaa ccgatcaggc tgcccactct gcttggaaat tgctgctcga acgcctggac | 180 |
| aattatctgc agaactttcg tggttggcag tgggtctatg cttccatgtc catcgtgaca | 240 |
| ttggctgcgg taggcgttat tatcgcatcc ggaaacatgg atgaaccttc tgaatcttac | 300 |
| gtatcctcca ccaaggataa ggaagaaata ctcctgacga aaaagccgt tcccgtaagt | 360 |
| aaggaaacta ttgaacgaac ctcaaccgaa gttgctccca cggaaaaacc tgaattcacc | 420 |
| acgggagact cttcatatga acatcggcc aaagacaacc agctgaaacc tgattcccat | 480 |
| gccgataaaa aaccggtatc ccgcgttctc attgagatgt aa | 522 |

<210> SEQ ID NO 43
<211> LENGTH: 603
<212> TYPE: DNA
<213> ORGANISM: Akkermansia muciniphila

<400> SEQUENCE: 43

```
atgacgtttg ggagtctctc acagagtgcc cttcctggcg gtttcattcc ttacggcggt    60
aattttatg cttccaatta cacgatctcc ctctggctgg atacctcttc cttaacggaa   120
ggaacccaga ccacgctgtt tgggtattat ggcaccaatg cgggccaaag ttacgggaca   180
aatgccttgt atctgacgac agatgccaag cttggcatgg agatggaaa tttggatact   240
tctaccggct ctttttccca aaaccgtgga cacgttctg aaactcccgt tgttttggag   300
ggaggtcttc ttaacgtgac tctagccgtt actggcgcag accaaagcca gtctgtggag   360
gtctatgtga atggttcctt gcttgacacg ttgtcctaca acggcaacat gaacggaaat   420
cgcactgata tccaaggatg gattaatccc aatcttacat ggggtgaaat tcagtggacg   480
gatacaaaac tttccgcgga acagattgcc ggttttgccg ccttcaggt tccggaaccg   540
gcctcggctt ctctgggaat cctgggcctg ccgttctga tgatgcgccg ccgccgttcc   600
tga                                                                603
```

<210> SEQ ID NO 44
<211> LENGTH: 330
<212> TYPE: DNA
<213> ORGANISM: Akkermansia muciniphila

<400> SEQUENCE: 44

```
atgaaaaaat tgatctatat gatagcggca gcggccgttg cgattccggt ggtggccctg    60
gcccagggag cctgcggcag cggctcctgc tccaagggag acaaggacat ggctgaagcc   120
aaagagcaca tgaaagaggg cgccaaggct gccaaggacg ccgcctccga aaaaatgaag   180
gaaggcaggc aggctgccag ggacgcctat gaaaagggca ggaaaccgc cagggatgct   240
tatcaggaca gcagggacgc cgttgaccat gcggcgaca ggactgccga taaggccgaa   300
gccgtcggtg acgctgtgaa aaacggttaa                                    330
```

<210> SEQ ID NO 45
<211> LENGTH: 1458
<212> TYPE: DNA
<213> ORGANISM: Akkermansia muciniphila

<400> SEQUENCE: 45

```
atgattccgc tccgcattgt tcttgcctcc ctggcatgcc tgtacccgtt ctctctggct    60
caggagccta atcggatcc cgataaaacg ctgattatca tttctaccag cgatatccac   120
ggcaatctgg acaatttccc aagactggcc acactggtaa agcaataccg cgctaaatat   180
ccgcacgtgc tgctggtgga ttcaggtgat tatttcatag caatccctat gtggacgac   240
tgtgaaaaac ggggcgaacc ccttactatc ctgatgaaca gctggggta tgatgtagtg   300
accatcggaa accatgatct ggattacggg caggaggccc tgcgcgacca tatcaaggga   360
atgccctcca ccaagtttgt cattaccaac gccagccttt ccccaactct ggaaaactgt   420
ttttctccgt atgtcagcat cccgattaaa ggaacgtcca tttccgtagg gtcatagga   480
ctggcagacc ttcaaaccac ggatgtgagg aggatgaccg gcatctcatg gaagctgccg   540
gatgaagaag actacaaggg aatcacggac aggttccggc tccaccataa taccatcaac   600
gtcatcctca gccatctggg atacggcaat gatctgaaaa tgatgaagta ttctccgaat   660
```

| | |
|---|---:|
| atcgacgtca ttcttggagg ccatacccat gtcatgctgc ccagcggtca tctcagaacc | 720 |
| ggaaccctgc tcagccacac gggacacagc ctgagccatg taggcgttac ggaaattatt | 780 |
| ttctccacgg aacatcccgt ctccatcctt tccaaatcaa ccagggccgt ttctttgaat | 840 |
| gaggaaattc ccgatgaccc ggaagtaaag gaaattgtcc gccgattttc cggaaatccg | 900 |
| cttttcaacc agcaagtggg cgtcgccgga aagaaatca cgcacgtcac cataggcacc | 960 |
| cttttctgca aggccattca gcaggcctcc cattcggata ttgccattta caaccgcggc | 1020 |
| ggagtacggt ccaaaaacca tcttaacaaa ggacccgtta ccatcaggga catttacgag | 1080 |
| ctggaaccct tccgggaaaa gatcgtcacc tgctccatga gtaaagcgga cattgaacaa | 1140 |
| ctgatcctgt ccaaattcat gtctccgacc gatgacgaag gaggcgttct ggaagtgtac | 1200 |
| tgctccggat tctcctacca gatcatggac ggtgttacgc ccagcattac cagcaccttg | 1260 |
| aaaaacgggg tcatttacac tgtcgcgatg ggagactacc tgtgcagcaa tttcatattc | 1320 |
| ccccaacggg ggaacggcaa accgacggga atagatgtcc gcaaagccct gattgattac | 1380 |
| ctgaaacaaa tcaaggagct gctcaatcct ccgccgtcca agctacctat catcaaagat | 1440 |
| acgacgttcg ccctgtga | 1458 |

<210> SEQ ID NO 46
<211> LENGTH: 789
<212> TYPE: DNA
<213> ORGANISM: Akkermansia muciniphila

<400> SEQUENCE: 46

| | |
|---|---:|
| atgaagaaat ccttgttgtc tttagcttta atctcaagta ccttgcttgc cgtagaggcg | 60 |
| gcaacggtgc aaattgattt cggacgcagt gacgccacga cggacggcgt gctcaatatg | 120 |
| aattatgata gtgcctccgc cgcttgggc agcatgccgg gaagcgtttc tttggcatgg | 180 |
| agtacggcag aatggcctgt aggggataat ggccatacca ccaccaagac agttgaggaa | 240 |
| gaagccgatt ggaaaaatcc tttcaacgg agcatgcctt tcagcttggg ggacactttt | 300 |
| cgtgacggtc ttttaacgca gacggccgac gggtccggct ctttcactgt aacgttcagc | 360 |
| ggtcttgccg ccggggagta ttccttgtcc atctttggag gtttcacagg caaggatgca | 420 |
| tttgccggtc aaacctggac gatcggaaac gccgatgctt ccaatgccgt ctggacaagc | 480 |
| ttcggcacag acgccagcgg gaactgggcc gaaatttctt ccgtgacggg cgataattcc | 540 |
| ggagtcctta ctccggcgaa cgcttccact tccagcgcta ctgctaataa agggctttat | 600 |
| gctacggtag agaatgtcgt ggtaggggaa gacgggacgc ttaccctttac gattcagggg | 660 |
| gatgggagca aggggtacgg ccttacagcc cttaattacc tttccctgac gcaggtgccg | 720 |
| gaacccgcta cggcagcatt gagcctgctg ggcgctgctg ccctgttcct gcgccgccgc | 780 |
| agggactga | 789 |

<210> SEQ ID NO 47
<211> LENGTH: 1190
<212> TYPE: DNA
<213> ORGANISM: Artificial Sequence
<220> FEATURE:
<223> OTHER INFORMATION: transposon insert from pSAM_Akk

<400> SEQUENCE: 47

| | |
|---|---:|
| taacaggttg gatgataagt ccccggtctt cgtatgccgt cttctgcttg gcgcgccctc | 60 |
| gagcaattgc gctcgtaaga ggttccaact ttcaccataa tgaaataaga tcactaccgg | 120 |
| gcgtattttt tgagttatcg agattttcag gagctaagga agctaaaatg gagaaaaaaa | 180 |

```
tcactggata taccaccgtt gatatatccc aatggcatcg taaagaacat tttgaggcat    240
ttcagtcagt tgctcaatgt acctataacc agaccgttca gctggatatt acggcctttt    300
taaagaccgt aaagaaaaat aagcacaagt tttatccggc ctttattcac attcttgccc    360
gcctgatgaa tgctcatccg gaattccgta tggcaatgaa agacggtgag ctggtgatat    420
gggatagtgt tcaccottgt tacaccgttt tccatgagca aactgaaacg ttttcatcgc    480
tctggagtga ataccacgac gatttccggc agtttctaca catatattcg caagatgtgg    540
cgtgttacgg tgaaaacctg gcctatttcc ctaaagggtt tattgagaat atgttttcg     600 tctcagccaa tccctgggtg agtttcacca gttttgattt aaacgtggcc aatatggaca    660
acttcttcgc ccccgttttc accatgggca aatattatac gcaaggcgac aaggtgctga    720
tgccgctggc gattcaggtt catcatgccg tttgtgatgg cttccatgtc ggcagaatgc    780
ttaatgaatt acaacagtac tgcgatgagt ggcagggcgg ggcgtaattt ttttaaggca    840
gttattggtg cccttaaacg cctggtgcta cgcctgaata agtatgcgag agtagggaac    900
tgccaggcat caaataaaac gaaaggctca gtcgaaagac tgggcctttc gttttatctg    960
ttgtttgtcg gtgaacgctc tcctgagtag gacaaatccg ccgggagcgg atttgaacgt   1020
tgcgaagcaa cggcccggag ggtggcgggc aggacgcccg ccataaactg ccaggcatca   1080
aattaagcag aaggccatcc tgacggatgg ccttttttgcg tttctacctg cagggcgcgc   1140
caagcagaag acggcatacg aagaccgggg acttatcatc caacctgtta              1190
```

SYSTEMS AND METHODS FOR GENETIC MANIPULATION OF *AKKERMANSIA* SPECIES

CROSS-REFERENCE TO RELATED APPLICATIONS

This application is the U.S. national phase of International Application No. PCT/US2019/032431 filed May 15, 2019, which designated the U.S. and claims priority to U.S. Provisional Application No. 62/671,614 filed on May 15, 2018, the contents of each of which are incorporated by reference in their entirety.

STATEMENT REGARDING FEDERALLY SPONSORED RESEARCH

This invention was made with Government support under Federal Grant No. 5R21DK110496-02 awarded by the NIH. The Federal Government has certain rights to this invention.

REFERENCE TO SEQUENCE LISTING AS TEXT FILE

The present application was filed with a Sequence Listing on Nov. 13, 2020, which was submitted electronically in ASCII format and is hereby incorporated by reference in its entirety. The ASCII copy of the Sequence Listing, created on Nov. 13, 2020, is named "155554-00578_SEQ_Listing.TXT" and is 82.5 KB (84,569 bytes) in size.

BACKGROUND OF THE INVENTION

The field of the invention is related to genetically modifying and selecting of gut microbes that have altered phenotypes and for use of these microbes in treating diseases.

*Akkermansia muciniphilia* are a bacteria found on the mucosal surface of the human intestinal track. This bacteria uses mucin as its single nutrient source. It accounts for 1-4% of the intestinal bacteria in adults and is a species of bacteria that inhabits the large intestine. It is a gram-negative, obligate, anaerobic, non-motile, nonspore-forming elliptical eubacterium that is thought to be beneficial to the gut flora. However, *Akkermansia* has been found to be difficult to molecularly manipulate. The mechanisms by which *Akkermansia* physiologically influences the gut microbiome, mucosal and systemic immunity and glucose/lipid metabolism is not well understood.

As such, there is a need for methods and systems for producing genetically altered *Akkermansia* strains to study its role in gut flora.

SUMMARY OF THE INVENTION

The present disclosure is based, in part, on the development of the inventors of a method to genetically alter *Akkermansia* bacteria using a transposon vector. Genetically altered *Akkermansia* bacteria and libraries of altered *Akkermansia* bacteria are also provided. Other aspects of the present disclosure are provided in all that is described and illustrated herein.

In one aspect, the disclosure provides a method of genetically altering *Akkermansia* bacteria, the method comprising: (a) introducing a exogenous transposon vector of SEQ ID NO:1 into *Akkermansia* to produce a plurality of altered *Akkermansia* bacteria; and (b) culturing the plurality of altered *Akkermansia* to select for bacterium having incorporated the transposon of the vector into the genome to produce a plurality of genetically altered *Akkermansia* bacteria.

In another aspect, the disclosure provides a genetically altered *Akkermansia* bacteria produced by the method described, wherein the genetically altered *Akkermansia* bacteria genome contains the transposon (SEQ ID NO:47) of the transposon vector (SEQ ID NO:1).

In another aspect, the disclosure provides a genetically altered *Akkermansia* bacteria produced by incorporating the transposon from vector of SEQ ID NO:1 into an *Akkermansia* bacteria. In one example, the transposon is SEQ ID NO:47 incorporated into the *Akkermansia* genome.

In another aspect, the present disclosure provides a library of altered *Akkermansia* bacteria, the library produced by randomly introducing a transposon from the vector of SEQ ID NO:1 into a population of *Akkermansia*, and selecting for the altered *Akkermansia* bacteria by culturing the bacteria under anaerobic conditions in medium containing chloramphenicol to select for *Akkermansia* that have the transposon inserted into their genome.

In yet another aspect, the present disclosure provides a method of selecting for an altered *Akkermansia* bacterium having an altered genetic regulator of a trait, the method comprising: (a) introducing an exogenous transposon vector of SEQ ID NO:1 into a population of *Akkermansia* to randomly incorporate the transposon into the *Akkermansia* genome; (b) culturing the population *Akkermansia* to select for *Akkermansia* having the transposon integrated into their genome to produce a plurality of altered variants of *Akkermansia*; and (c) selecting for *Akkermansia* having the altered genetic regulator by culturing the *Akkermansia* under conditions in which the altered genetic trait is selected.

In another aspect, the disclosure provides a method of identifying novel genetic regulators of a trait in *Akkermansia*, the method comprising: (a) incorporating an exogenous transposon vector of SEQ ID NO:1 into a population of *Akkermansia* to produce a population of altered *Akkermansia* incorporating the transposon into their genome; (b) culturing the *Akkermansia* in medium comprising chloramphenicol to select for *Akkermansia* having incorporated the exogenous transposon; (c) exposing the altered *Akkermansia* to two different conditions; and (d) analyzing by sequencing or PCR amplifying the genes disrupted by the transposon in the altered *Akkermansia* grown under the two different conditions to identify genes associate with the trait.

The foregoing and other aspects and advantages of the invention will appear from the following description. In the description, reference is made to the accompanying drawings which form a part hereof, and in which there are shown, by way of illustration, preferred embodiments of the invention. Such embodiments do not necessarily represent the full scope of the invention, however, and reference is made therefore to the claims and herein for interpreting the scope of the invention.

DETAILED DESCRIPTION OF THE INVENTION

Figure 1:
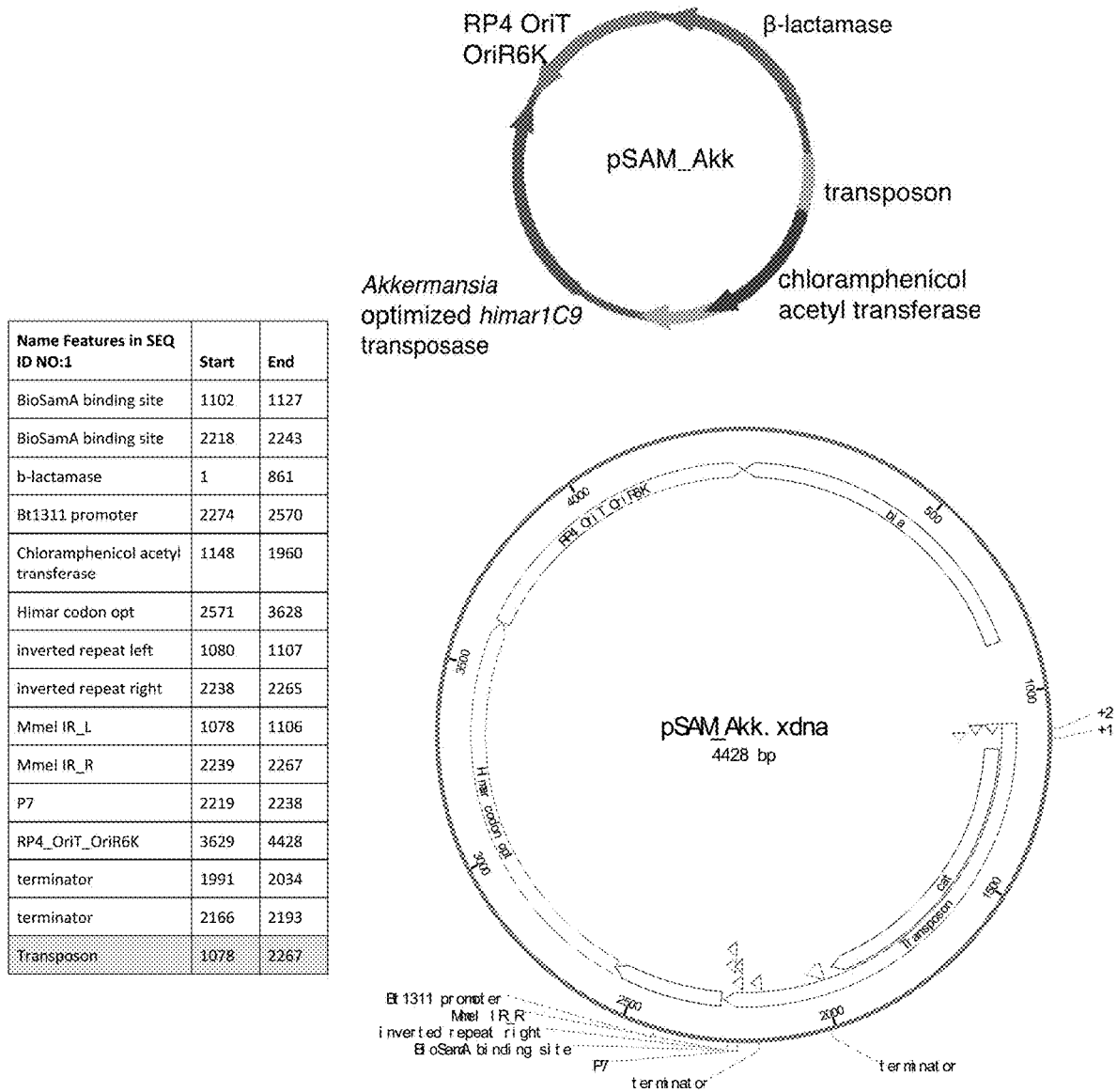
FIG. 1. The *Akkermansia* compatible transposon vector pSAM_Akk.

The present invention has been described in terms of one or more preferred embodiments, and it should be appreciated that many equivalents, alternatives, variations, and modifications, aside from those expressly stated, are possible and within the scope of the invention. Before the present invention is described, it is understood that this invention is not limited to the particular methodology, protocols, and reagents described, as these may vary. It is also to be understood that the terminology used herein is for the purpose of describing particular embodiments only, and is not intended to limit the scope of the present invention which will be limited only by the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result. The term about as used herein refers to a range of +/−10% of the numerical value listed.

The use herein of the terms "including," "comprising," or "having," and variations thereof, is meant to encompass the elements listed thereafter and equivalents thereof as well as additional elements. Embodiments recited as "including," "comprising," or "having" certain elements are also contemplated as "consisting essentially of and "consisting of" those certain elements.

Recitation of ranges of values herein are merely intended to serve as a shorthand method of referring individually to each separate value falling within the range, unless otherwise-Indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition.

The term "effective amount" or "therapeutically effective amount" refers to an amount sufficient to effect beneficial or desirable biological and/or clinical results.

As used herein, the term "subject" and "patient" are used interchangeably herein and refer to both human and nonhuman animals. In a preferred embodiment, the subject or patient is a human. The term "nonhuman animals" of the disclosure includes all vertebrates, e.g., mammals and non-mammals, such as nonhuman primates, mouse, rat, sheep, dog, cat, horse, cow, chickens, amphibians, reptiles, and the like. In some embodiments, the subject is a mouse, or a mouse model of a disease.

Methods

The present disclosure provides, in part, materials, systems and methods for the mutation and characterization of the gut microbe *Akkermansia muciniphila* and related species (including clinical strains) and uses thereof of the altered *Akkermansia*.

The present disclosure provides tools and methods to genetically manipulate the emerging pro-biotic *Akkermansia muciniphila*. The systems and methods allow for rapidly identifying factors related to a phenotypic trait, for example, factors mediating colonization of animals, including new enzymes mediating the breakdown of mucins and successful competition with other members of the microbiota. The systems allow for the generation of altered strains that are better suited as immunomodulators of chronic inflammation and with enhanced properties as protectors against diet-induced obesity and boosters of cancer immunotherapies.

The inventors have developed a method to genetically modify *Akkermansia muciniphila* that incorporates transposon mutagenesis (insertion of a transposon from a vector into the *Akkermansia* genome), phenotype analysis and PCR or sequenced-based mutational mapping to identify novel genetic regulators in *Akkermansia* found in the human microbiome in the intestine.

*Akkermansia muciniphila* is a Gram-negative, strictly anaerobic, non-motile, non-spore-forming, oval-shaped bacterium found in the gut microbiome. Prior to this disclosure *A. muciniphila* was not known to be amenable to molecular genetic manipulation. They are known to process mucin, a glycosylated protein important in luminal protection of the gastrointestinal track.

The availability of carbohydrates in the gastrointestinal track plays a role in shaping the structure-function of the microbiota and determination of which microbes can grow and colonize the intestinal track. Utilization of microbes in promoting health is relies on the ability to colonize useful bacteria within the gut to maintain a healthy flora. There is still little known about the structural requirements for mucin degradation by gut bacteria and the limited functional characterization of enzymes that correlate with the strains able to degrade and utilize mucin and mucin glycans. Mucin is a large, highly glycosylated proteins. The present disclosure provides methods of making altered variants of *Akkermansia*, populations of altered *Akkermansia*, and use of the altered *Akkermansia* to colonize the colon and promote health in a subject.

In one aspect, the present disclosure provides a method of genetically altering an *Akkermansia* bacterium, the method comprising: (a) introducing an exogenous transposon vector of SEQ ID NO:1 into *Akkermansia* to produce an altered *Akkermansia* bacterium; and (b) culturing the altered *Akkermansia* to select for *Akkermansia* having incorporated the transposon into the genome. In another aspect, the present disclosure provides a method of genetically altering *Akkermansia* bacteria, the method comprising: (a) introducing an exogenous transposon vector of SEQ ID NO:1 into *Akkermansia* to produce a plurality of altered *Akkermansia* bacteria comprising the transposon; and (b) culturing the plurality of altered *Akkermansia* to select for bacteria having incorporated the transposon into the genome to produce a plurality of genetically altered *Akkermansia* bacteria.

Methods of introducing an exogenous transposon vector of SEQ ID NO:1 into *Akkermansia* to produce a plurality of altered *Akkermansia* bacteria are known in the art. These methods are generally referred to as transposon mutagenesis or transposition mutagenesis and allows for genes to be transferred to a host organism's chromosome, interrupting or modifying the function of the extant gene on the chromosome and causing mutation. This allows for the ability to induce single hit mutations within a genome, and the ability to identify the gene that has been mutagenized by being able to identify the adjacent sequences to the transposon. The transposon vector of SEQ ID NO:1 has been specifically designed for use in *Akkermansia* as described in Example 1. The vector of SEQ ID NO:1 contains a modified mariner transposon, himar1C9, with a chloramphenicol resistance cassette (cat) and the transposase enzyme required to catalyze transposition. The vector further comprises lamba pir dependent origin of replication and is unable to replicate in strains such as *Akkermansia* that lack pir genes.

The transposon vector (SEQ ID NO:1) comprises the transposon (nucleic acids 1078-1145 of SEQ ID NO:1 (e.g. SEQ ID NO:47) and the transposase enzyme. The transposase enzyme is required for extracting and inserting the transposon into the *Akkermansia* genome. Once transposition occurs, the transposon (SEQ ID NO:47 (nucleic acids 1078-1145 of SEQ ID NO:1) are inserted into the genome of the altered *Akkermansia* strain. Thus, the altered *Akkermansia* strain/variants comprises the transposon of SEQ ID NO:1. In other words, the altered *Akkermansia* strain/variants comprises SEQ ID NO:47 within its genome, but does not contain the rest of the transposon vector backbone.

The transposon vector contains the antibiotic resistance gene for chloramphenicol (cat) within the transposon, which was required for the use in *Akkermansia*, as prior vectors that used erythromycin as the antibiotic selection did not work in *Akkermansia* and resulted in spontaneous resistance.

One method of introducing the transposon vector into *Akkermansia* is by conjugation. Methods of conjugation are known in the art and for example, but not limited to, the method as described in Example 2. Bacterial conjugation is the transfer of genetic material (e.g., the exogenous transposon vector of SEQ ID NO:1) between bacterial cells by direct cell-to-cell. In a preferred embodiment, the transposon vector is conjugated from an *E. coli* strain to the *Akkermansia*. The method of conjugating includes co-culturing the *E. coli* strain carrying the transposon vector (e.g., SEQ ID NO:1) with *Akkermansia* under aerobic conditions for about 7-14 hours at 37° C.

Following conjugation, to counter select against *E. coli* and allow transposition to occur, the transconjugates were sub-cultured. Suitable methods of subculturing are known in the art. For example, as described in Example 2, the transconjugates are subcultured multiple times, for example 3 times, under anaerobic conditions. This allowed for the selection for the altered (variant strains) of *Akkermansia* that have incorporated the transposon (e.g. SEQ ID NO:47 corresponding to nucleic acids 1078-1145 of SEQ ID NO:1) into their genome from the other bacterial strains in the culture. This subculturing conditions are anaerobic conditions, and include a sub-culturing step in medium comprising chloramphenicol, the antibiotic resistance gene that is included in the transposon sequence.

Once subcultured, a population of altered *Akkermansia* comprising the transposon (including the antibiotic resistance gene) in their genome are produced. This population of altered *Akkermansia* can be grown and used as a library of altered *Akkermansia* for screening and treatment purposes. The library of altered (mutant variants of) *Akkermansia* can be used to screen for phenotypic traits. For example, in one embodiment, the library can be grown under conditions related to the phenotypic trait and screened to identify genes associated with the phenotypic trait.

The library of altered *Akkermansia* stains can also be used to characterize each altered *Akkermansia* strain by DNA sequencing or PCR analysis of the genomic sequence adjacent to the transposon inserted into the genome. This allows for determination of which gene has been altered by the insertion of the transposon.

In one embodiment, the method further comprises: culturing the plurality of genetically altered *Akkermansia* under conditions to select for a trait; and identifying the gene associated with the trait by PCR or sequencing of the gene adjacent to the transposon within the *Akkermansia* genome.

Methods of DNA sequencing to identify the genes disrupted by the transposon are known in the art. For example, in one embodiment, the DNA sequencing method used can be INSeq/TnSeq as described in Goodman et al. (Nat. Protoc.: 6(12): 1969-1980 (2012), doi:10.1038/nprot2011.417), the contents of which are incorporated by reference in its entirety. Briefly, Insertion Sequencing (INSeq) is a method for determining the insertion site and abundance of transposon mutants in a mixed population using a modified mariner transposon containing MmeI sites at its ends, allowing for the cleavage at chromosomal sites 16-17 bp from the inserted transposon. See Goodman et al. abstract. Genomic regions that are adjacent to the transposons are amplified by linear PCR, and sequenced using a high-throughput instrument as described in Goodman.

The present disclosure contemplates a library of genetically altered *Akkermansia*, specifically, a library of genetically altered *Akkermansia muciniphila*. Further, libraries of genetically altered *Akkermansia* made from clinical strains of *Akkermansia* (e.g. strains isolated from a patient, for example, but not limited to, an obese patient, patient with chronic inflammation, among others). The library can be used for screening and culturing of altered *Akkermansia* that play a role in phenotypic traits.

In another embodiment, the disclosure provides a library of altered *Akkermansia* bacteria produced by randomly introducing a transposon from the vector of SEQ ID NO:1 into a population of *Akkermansia* and selecting for the altered *Akkermansia* bacteria by culturing the bacteria under anaerobic conditions in medium containing chloramphenicol to select for *Akkermansia* that have the transposon inserted into their genome. The term "library' is used in reference to and used interchangeably with a plurality of altered *Akkermansia* bacteria.

As used herein, the terms "altered *Akkermansia*," "altered *Akkermansia* strain", "genetically altered *Akkermansia*,", "variants of *Akkermansia*," "Tn mutant *Akkermansia*," "Tn mutants," and "mutant *Akkermansia*" are used interchangeably to refer to the genetically modified *Akkermansia* that have incorporated the transposon of the transposon vector of SEQ ID NO:1 into their genome. Tn mutants refer to mutant strains made by insertion of a transposon (Tn) as noted in the art. The *Akkermansia* may be any known species of *Akkermansia* that falls within the genus, including, but not limited to, for example, *Akkermansia muciniphila* or clinical species isolated from patients.

For example, the library of altered *Akkermansia* strains can be used in method of screening for genes required for the utilization of mucin. In some embodiments, a library of genetically altered *Akkermansia* are cultured in medium with or without mucin. The library grown without mucin can be compared genetically to the library grown in medium containing mucin. Methods of genetically analyzing the genes in the altered *Akkermansia* grown in the presence of mucin and the genes in altered *Akkermansia* grown in the absence of mucin can be determined by sequence or PCR analysis, as detailed herein, and the genes from the two populations compared to identify genes that regulate mucin utilization. This is demonstrated in Example 3 herein.

In some embodiments, altered *Akkermansia* strain that has advantageous growth characteristics in the presence of mucin can be identified. These altered *Akkermansia* with advantageous growth characteristics can be used to colonize a subject's colon by administering the altered *Akkermansia* to the subject.

Suitable methods of administering the altered *Akkermansia* strains to a subject are known in the art, and include, administering the altered *Akkermansia* orally, rectally, or other routes that maintain the viability of the bacteria. In some embodiments, the altered stain can be administered orally, for example, but not limited to, in tablets, capsules, liquids, etc. that allow for delivery of the strains to the intestinal track. Suitably, the altered strains may be formulated into a composition that allows for the strain to maintain viability while being delivered to the intestinal track.

In another embodiment, the library of altered *Akkermansia* can be screened for phenotypic traits associated with stable colonization of the intestine. In some embodiments, the method comprises: introducing the plurality of genetically altered *Akkermansia* into a subject, and detecting the altered *Akkermansia* that have a growth advantage colonizing the intestine of the subject by genetically analyzing the genes in the altered bacteria growing within the colon of the subject. In some embodiments, the bacteria that are colonizing the intestine of the subject are obtained in a sample from the colon of the subject, culturing the sample under conditions suitable for growth of the altered *Akkermansia* (e.g. anaerobic conditions in the presence of chloramphenicol to select for *Akkermansia* with the transposon), and identifying the genes associated with the growth advantage by sequencing or PCR analysis of the altered *Akkermansia* strains grown. Suitably, DNA sequencing or PCR methods used to determine genes associated are specific to the transposon (e.g. use primers specific to the exogenous transposon) and thus allow for identification of the genetically altered *Akkermansia* strains that have the transposon as opposed to any wildtype bacteria that may be growing within the gut. In some embodiments, the subject is a mouse. In some embodiments, the subject is a mouse model of a disease (e.g., obesity mouse model, etc.).

The methods described herein can be used in methods of screening for other phenotypical traits. For example, the Tn/IN-seq to screen for variants with enhanced colonization under various diets/disease conditions. This can be done by feeding the subject a specific diet, and screening for the ability of the altered bacteria to colonize the colon under the specific diet conditions or under immune-status alteration. This can identify altered bacteria that have genes that specifically breakdown and utility the components of the diet.

In another embodiment, the methods described herein can be used to screen for genes involved in phenotypes that could affect colonization and interaction with host, for example biofilm formation, aggregation, capsule production, IgA binding, and resistance to antimicrobial peptides or bile salts. In some examples, the phenotype trait may be, for example, but not limited to, amino acid biosynthesis, carbohydrate metabolism, nutrient uptake, redox tolerance, adherence, invasion, growth, reproduction, and the like. A trait can include a genetically-determined characteristic that is important for the overall growth and survival of that bacteria, such as the ability to colonize the host intestine. For example, as demonstrated in the examples, some genetic regulators of *Akkermansia* growth include genes that are required for utilization of mucin, e.g., genes found in Table 1. Other genes necessary for the growth and colonization of *Akkermansia* in the colon including the distal colon of a subject are found in Table 3. The present disclosure is not limited to these genes as these are exemplary of what can be identified by the methods described herein.

In a further embodiment, the mutants can be screened for genes involved in activating host signaling pathways, for example the TLR2 signaling pathways that have been linked to intestinal health and prevention of obesity. For example, in one embodiment, the method involves screening for altered *Akkermansia* strains that have different levels of TLR2-mediated recognition by immune cells, or in another embodiment, administering the altered *Akkermansia* to a subject normal and obese subject (e.g., normal and obese mouse model) both being fed the same diet (e.g. normal or high fat), and screening for the genes associated with the bacteria within the obese subject compared to the non-obese subject.

In another aspect, the disclosure provides a method of selecting for an altered *Akkermansia* bacterium having an altered genetic regulator of a trait, the method comprising: (a) introducing an exogenous transposon vector of SEQ ID NO:1 into a population of *Akkermansia* to randomly incorporate the transposon into the *Akkermansia* genome; (b) culturing the population *Akkermansia* to select for *Akkermansia* having the transposon integrated into their genome to produce a plurality of altered variants of *Akkermansia*; and (c) selecting for *Akkermansia* having the altered genetic regulator by culturing the *Akkermansia* under conditions in which the altered genetic trait is selected. In some aspects, step (a) comprises conjugation of the *Akkermansia* with *E. coli* containing the transposon vector of SEQ ID NO:1. In further aspects, the methods of step (b) comprises subculturing the bacteria under anaerobic conditions to select for the altered variants of *Akkermansia* in the presence of chloramphenicol. Methods of determining the altered genetic regulator can be done by methods known in the art, including, but not limited to, sequencing (e.g., but not limited tom INSeq/TnSeq described in Goodman et al. 2011), or PCR analysis of the genome adjacent to the transposon element.

In another embodiment, the present disclosure provides a method of identifying novel genetic regulators of a trait in *Akkermansia*, the method comprising: (a) incorporating an exogenous transposon vector of SEQ ID NO:1 into a population of *Akkermansia* to produce a population of altered *Akkermansia* incorporating the transposon into their genome; (b) culturing the *Akkermansia* in medium comprising chloramphenicol to select for *Akkermansia* having incorporated the exogenous transposon; (c) exposing the altered *Akkermansia* to two different conditions; and (d) analyzing by sequencing or PCR amplifying the genes disrupted by the transposon in the altered *Akkermansia* grown under the two different conditions to identify genes associate with the trait.

Another aspect of the present disclosure provides a system that comprises a discovery platform using a transposon vector for genetically manipulating *Akkermansia* bacteria, including the probiotic *Akkermansia muciniphila* for the treatment of chronic inflammation in a subject.

In some aspects, genetically manipulating the probiotic *Akkermansia muciniphila* for the treatment of treatment of diet-induced obesity in a subject.

In another aspect, the genetically altered *Akkermansia* can be used to boost immune checkpoint inhibitors in cancer immunotherapies. This can be done by administering an effective amount of the altered *Akkermansia* (e.g., altered *Akkermansia muciniphila*) in a subject undergoing checkpoint inhibitor therapy to enhance the anti-cancer properties of the checkpoint inhibitor (See, e.g., Routy et al., Science 359, 91-97 (2018)).

Methods of enhancing checkpoint inhibitor therapy are contemplated. The methods comprising administering an effective amount of the altered *Akkermansia* (e.g., altered *Akkermansia muciniphila*) in a subject undergoing checkpoint inhibitor therapy to enhance the anti-cancer properties of the checkpoint inhibitor. For example, in one embodiment, the altered *Akkermansia* (e.g., altered *Akkermansia muciniphila*) can be used to increase the efficacy of PD-1 based immunotherapies (e.g., PD-1 antibody (i.e., pembrolizumab, nivolumab, cemiplimab, etc. which are commercially available, for example, pembrolizumab, and anti-PD-1 antibody, available from Merck and Co and described in U.S. Pat. Nos. 8,952,136, 83,545,509, 8,900,587 and EP2170959; nivolumab, an anti-PD-1 antibody, available from Bristol-Myers Squibb Co and described in U.S. Pat. Nos. 7,595,048, 8,728,474, 9,073,994, 9,067,999, 8,008,449 and 8,779,105).

In one embodiment, methods of treating diet-induced obesity are contemplated. The methods comprise administering an effective amount of an altered *Akkermansia* strain to the subject in order to treat the diet-induced obesity. In one embodiment, the altered *Akkermansia* strain has an altered gene selected from Table 3.

In another aspect, the disclosure provides methods of treating an inflammatory disorder, the method comprising administering an effective amount of an altered *Akkermansia* strain to treat the inflammatory disorder.

Other aspects of the present disclosure provide for using the systems and methods described herein for genetically manipulating the emerging pro-biotic *Akkermansia muciniphila* to generate strains that are better suited as immunomodulators of chronic inflammation and with enhanced properties as protectors against diet-induced obesity.

The present disclosure also contemplates a genetically altered *Akkermansia* bacteria containing the transposon from SEQ ID NO:1.

In another aspect, the present disclosure contemplates a genetically altered *Akkermansia* bacteria which has a disruption of any one of the genes listed in Table 1. These genetically altered *Akkermansia* bacteria have genes altered in the ability to utilize mucin.

In another embodiment, the present disclosure contemplates a genetically altered *Akkermansia* bacteria has disruption of any one of the genes listed in Table 2. These genetically altered *Akkermansia* bacteria have genes required for the utilization of mucin. In another embodiment, the present disclosure contemplates a genetically altered *Akkermansia* bacteria has disruption of any one of the genes listed in Table 3. These genetically altered *Akkermansia* bacteria have genes that provide a growth advantage in colonizing the colon of a subject. Methods of using any of the contemplated genetically altered *Akkermansia* bacteria having one or more of the genes listed in the table disrupted is contemplated for use in administering to a subject.

In some embodiments, kits for carrying out the methods described herein are provided. The kits provided may contain the necessary components with which to carry out one or more of the above-noted methods.

In one embodiment, the kit comprises the vector of SEQ ID NO:1 and instructions for transposition within a bacteria. In some embodiments, the kit comprises instructions on how to isolate and alter a strain of *Akkermansia*, including, but not limited to, *Akkermansia muciniphila* or a related species, including clinical strains.

In another embodiment, the kit comprises an altered *Akkermansia muciniphila* strain comprising the transposon of SEQ ID NO:1.

The present invention has been described in terms of one or more preferred embodiments, and it should be appreciated that many equivalents, alternatives, variations, and modifications, aside from those expressly stated, are possible and within the scope of the invention.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. The term "consisting essentially of" and "consisting of" should be interpreted in line with the MPEP and relevant Federal Circuit interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim. For example, with regard to sequences "consisting of" refers to the sequence listed in the SEQ ID NO. and does refer to larger sequences that may contain the SEQ ID as a portion thereof.

All publications, patent applications, patents, and other references mentioned herein are incorporated by reference in their entirety. In the case of conflict, the present specification, including definitions, will control. In addition, the materials, methods, and examples are illustrative only and not intended to be limiting.

The systems and methods provided herein have many commercially important biological from microbial communities associated with humans, livestock and industrial settings.

The invention will be more fully understood upon consideration of the following non-limiting examples.

EXAMPLES

Example 1: Modified Tn Mutagenesis Vector for Use in *Akkermansia*: pSAM_Akk

To be able to do genetic screening for genes and altered bacteria with altered phenotypes, a tool for mutating the bacteria was necessary. A modified version of a previously described vector was generated for use in *Akkermansia*. The original vector, pSAM_Bt[1], was designed for use in *Bacteroides thetaiotaomicron*. The vector encodes both a modified mariner transposon, himar1C9, with an erythromycin resistance gene and the transposase enzyme required to catalyze transposition. The plasmid uses a lamba pir dependent origin of replication and is unable to replicate in strains such as *Akkermansia* that lack pir genes.

To make pSAM_Bt compatible for use in *Akkermansia*, the original erythromycin resistance marker on the transposon (ermG) was replaced with a chloramphenicol resistance cassette (cat). Initial attempts to use erythromycin as a selection marker in *Akkermansia* were unsuccessful and growth with erythromycin repeatedly resulted in spontaneous resistance. The transposase enzyme was then codon optimized for expression in *Akkermansia*. We generated an *Akkermansia* codon table by concatenating a series of housekeeping genes to make a 22 628 bp sequence to use as an input for codon analysis. Rare codons in the himar1C9 sequence were replaced codons used preferentially in *Akkermansia*. The resulting plasmid was named pSAM_Akk (FIG. 1, SEQ ID NO:1). We found that these alterations to the vector were essential for mutagenesis in *Akkermansia*, and alteration of the resistance marker or the transposase alone was insufficient for transposition to occur. Similarly, we have not had success using *Akkermansia* promoters to drive the expression of himar1C9. As such, pSAM-Akk vector has been specifically made to allow for mutagenesis of *Akkermansia muciniphila*.

Example 2: Methods for Mutagenesis and Transposon (Tn) Library Construction

The transposon vector (SEQ ID NO:1) was introduced into *Akkermansia* by conjugation with an *E. coli* donor strain. *Akkermansia* starter cultures sub-cultured 1:5 into 30 ml synthetic medium[2] and grown to OD600=0.6-1.0. The cells were then harvested by centrifugation in 1.5 ml tubes at 10 000×g, 5 min, 4° C. In parallel, *E. coli* S17 pSAM_Akk cultures were grown aerobically in LB+100 ug/ml ampicillin, 35 ug/ml chloramphenicol at 37° C. 200 rpm to an optical density (OD) OD600=0.4-0.7. To avoid shearing conjugation pili, *E. coli* was centrifuged at 2 000×g, 3 min, and washed once with sterile PBS. The *E. coli* and *Akkermansia* pellets were combined in a total volume of 0.5 ml in synthetic medium and the suspension was used to make 100 μl puddles on pre-reduced synthetic medium plates. The plates were incubated aerobically at 37° C. for 7-14 h depending on the *Akkermansia* strain. Aerobic incubation is critical for successful conjugation.

Figure 2:
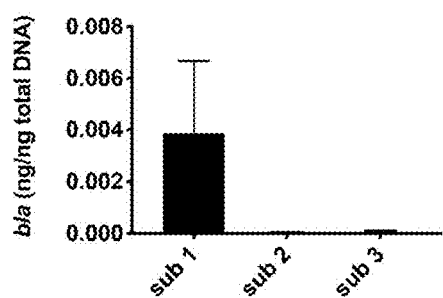
FIG. 2. The pSAM_Akk transposon inserts into the *Akkermansia* genome. (A) Quantitative PCR to detect the bla gene on the plasmid backbone following rounds of subculturing transconjugants. These subculturing steps are required to counter select for *E. coli*, to cure the plasmid, and for transposition to occur. (B) Southern blot of HindIII digested genomic DNA from wild-type*Akkermansia* and transposon mutants reacted with a dioxygenin-labeled transposon specific probe. (C) PCR to detect *Akkermansia* specific 16S rDNA (Akk), plasmid backbone (bla), and the drug resistance marker within the transposon (cat).
Figure 2:
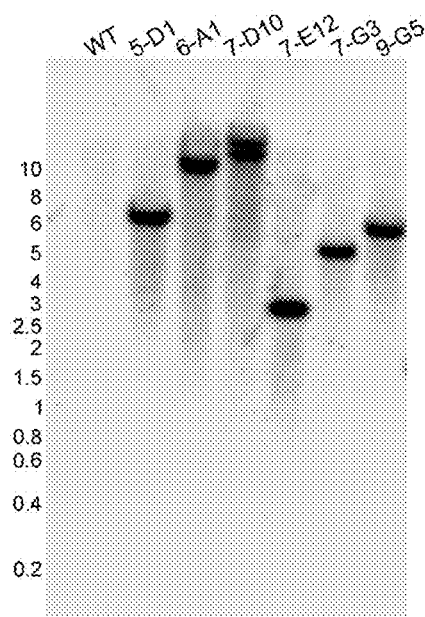
Figure 2:
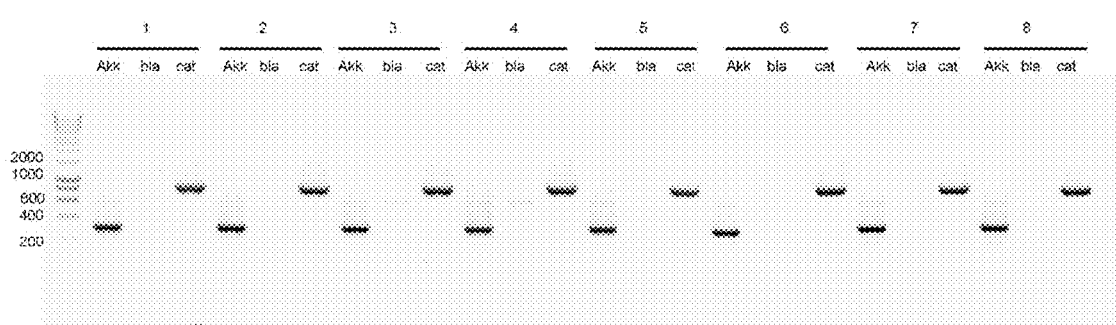

Following conjugation, the plates were transferred to an anaerobic chamber and the cells were scraped into 5 ml of a 1:1 mix of PBS and 50% glycerol (glycerol is optional but required to store cultures at −80° C.). To counter select against *E. coli* and allow transposition to occur, the transconjugants were sub-cultured three times. A 200 μl aliquot of the cell suspension was used to inoculate 3 ml synthetic medium with 12 μg/ml kanamycin and 10 μg/ml gentamicin and incubated at 37° C., anaerobic, 48 h. The culture was then sub cultured two more times as described above at 24 h intervals. These sub-culturing steps are required to cure the plasmid and obtain transposon mutants (FIG. 2A). After the third round of sub-culturing, 100-200 μl of culture was spread on synthetic medium agar plates supplemented with 10 μg/ml gentamicin, 12 μg/ml kanamycin, and 7 μg/ml chloramphenicol, and incubated anaerobically at 37° C. for 6 days. This medium is required to inhibit the growth of residual *E. coli*. Once transconjugants have grown, single colonies were picked with a pipette tip and arrayed into 96-well plates containing with 200 μl per well synthetic medium with 10 μg/ml gentamicin, 12 μg/ml kanamycin, and 7 μg/ml chloramphenicol and incubated anaerobically at 37° C. for 3 days.

To confirm that the transposon had inserted into the genome, PCR for the (3-lactamase gene was used to test for the absence of the plasmid backbone (bla) and for the presence of the transposon (cat). Finally, a Southern blot was performed on a subset of mutants to confirm the Tn insertion had occurred as aa single insert and at multiple locations in the genome (FIGS. 2B and 2C).

Figure 3:
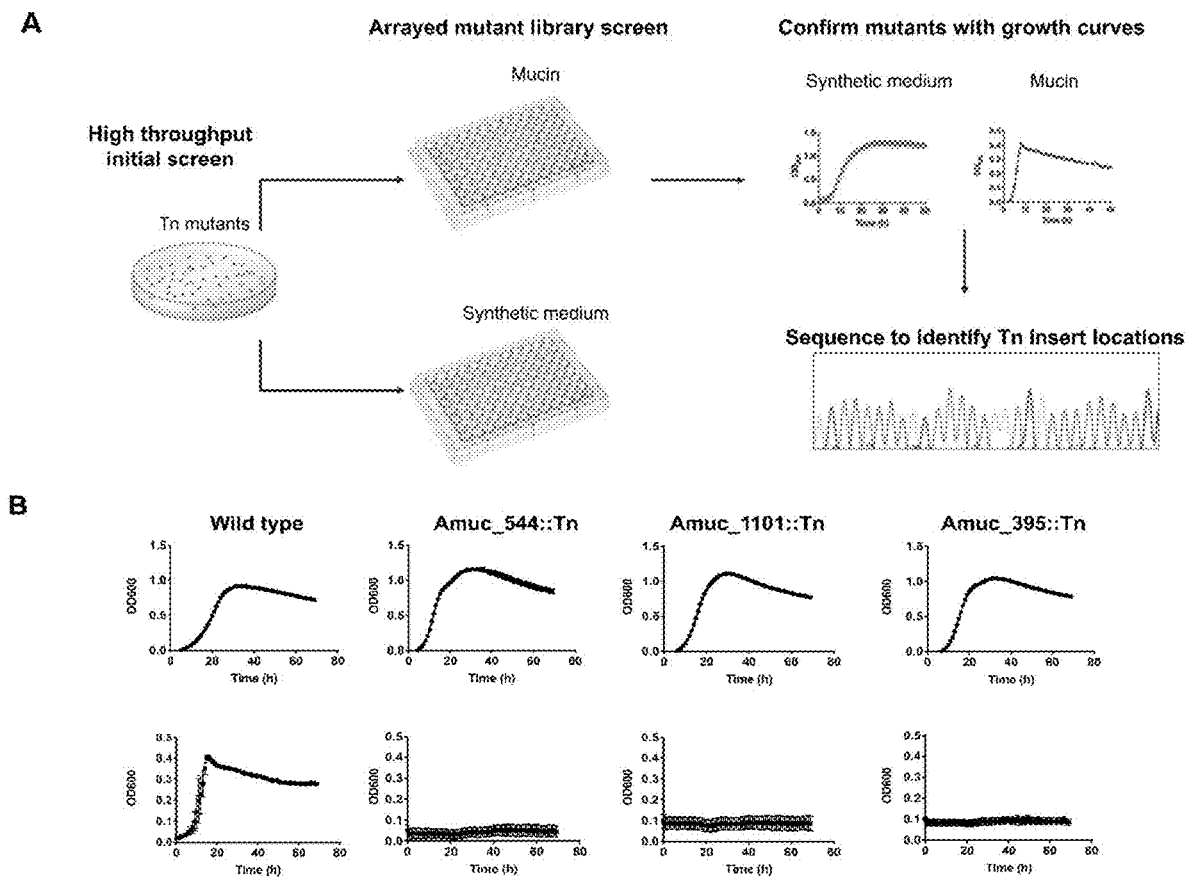
FIG. 3. Arrayed mutant screen for genes required for mucin utilization. (A) Approach used to identify genes required for growth on mucin. Following conjugation, Tn mutants are grown on plates with antibiotic selection and individual colonies were arrayed and grown in 96-well plates. The mutants were then used to inoculate plates containing media with either mucin or monosaccharides as the carbon source. Tn mutants that grew in synthetic medium, but not mucin, were selected for additional phenotypic characterization and PCR to identify the Tn insert location. (B) Growth curves of wild type *Akkermansia* and selected mutants. The mutants exhibit mucin-specific growth defects.

Example 3: Transposon Mutant Screens—Screening Transposon Mutants for Genes Required for Mucin Utilization To screen for genes required for mucin utilization, arrayed Tn mutants were used to inoculate duplicate 96-well plates containing either mucin medium[3] or synthetic medium. The plates were incubated anaerobically at 37° C. for 3 days. Following growth, the OD600 was measured using a plate reader. Mutants that grew in synthetic medium, but not in mucin, were selected for additional characterization. To confirm the initial screen, mutants of interest were tested for mucin growth defects by running growth curve assays in a plate reader, taking measurements every 60 min for 72 h (FIG. 3). Arbitrary PCR was used to locate the transposon insert sites and to identify the genes required for growth on mucin. The screen led to the identification of genes specifically required for growth on mucin, but not on monosaccharides (Table 1).

suspension was diluted 1:10 into synthetic media and incubated anaerobically at 37° C. for 36 h (this growth step is optional). The cultures were then washed once with sterile PBS and concentrated 10-fold, for a final concentration of approximately $10^{10}$ CFU/ml. The cell suspension was used to gavage germ free C57BL/6 mice with ~$10^8$ CFU. After one week of colonization, the mice were euthanized and the cecal contents were collected for DNA isolation. The DNA

TABLE 1

Genes identified as being required for growth on mucin

| Gene | Accession number gene/protein | Gene SEQ ID Nos: | Predicted protein function |
|---|---|---|---|
| Amuc_0029 (AMUC_RS00160) | ACD03876/NC_010655.1 (37306 . . . 38232, complement) | SEQ ID NO: 2 | UDP-glucose 4-epimerase |
| Amuc_0354 | ACD04193/NC_010655.1 (417915 . . . 419204, complement) | SEQ ID NO: 3 | Outer membrane efflux porin |
| Amuc_0394 | ACD04233/NC_010655.1 (476127 . . . 476885, complement) | SEQ ID NO: 4 | N-methyl domain protein |
| Amuc_0543 | ACD04381/NC_010655.1 (641820 . . . 642842, complement) | SEQ ID NO: 5 | TPR |
| Amuc_0544 | ACD04382/NC_010655.1 (642890 . . . 646123, complement) | SEQ ID NO: 6 | TPR |
| Amuc_1101 | ACD04927/CP001071.1 (1315394 . . . 1317178, complement) | SEQ ID NO: 7 | Type iv pilis protein/FtsA |
| Amuc_1102 | ACD04928/NC_010655.1 (1317279 . . . 1317995, complement) | SEQ ID NO: 8 | Hypothetical protein |
| Amuc_1229 | ACD05054/CP001071.1 (1477983 . . . 1478759, complement) | SEQ ID NO: 9 | IncA-like |
| Amuc_1246 | ACD05071/NC_010655.1 (1495432 . . . 1496679, complement) | SEQ ID NO: 10 | PA14 domain protein |
| Amuc_1443 | ACD05265/NC_010655.1 (1732600 . . . 1733982) | SEQ ID NO: 11 | TPR |
| Amuc_1486 | ACD05308/NC_010655.1 (1776309 . . . 1776770, complement) | SEQ ID NO: 12 | Hypothetical protein |
| Amuc_1523 | ACD05344/NC_010655.1 (1823279 . . . 1824025) | SEQ ID NO: 13 | Pili |
| Amuc_1524 | ACD05345/CP001071.1 (1824058 . . . 1824858, complement) | SEQ ID NO: 14 | N-methyl pili |

Example 4: Screening Transposon Mutants for Genes Required for Intestinal Colonization A second approach used to screen the Tn mutants was to create a large pooled library for use in for transposon insertion sequencing (Tn/IN-seq)[1]. This method identifies conditionally essential genes by passaging large pools of mutants though various conditions and subsequently using next-generation sequencing to test the abundance of each mutant in the input and output pools. Genes required for survival in the specific conditions will be depleted from the input pool. We used Tn/IN-seq to identify genes required for colonization of the mouse intestinal tract.

To create the pooled library, equal volumes of the arrayed Tn mutants were pooled into a single suspension. The cell was then used to prepare sequencing libraries following the protocol described by Goodman et al., with a modified primer set to allow for sequencing on Illumina's Hiseq 4000 platform.

Figure 4:
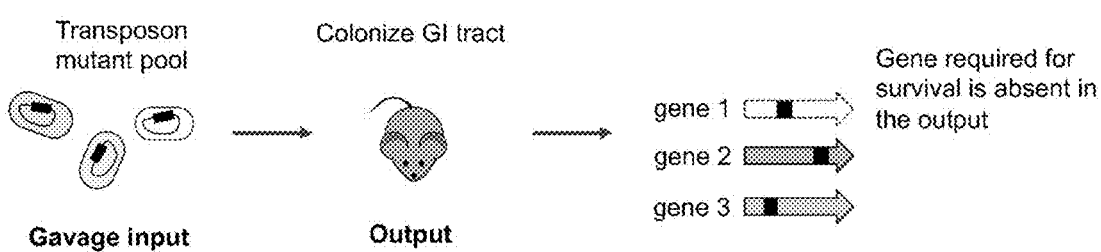
FIG. 4. Large scale genetic screens in vivo using Tn/INseq. (A) *Akkermansia* Tn mutants were pooled and used to colonize germ free mice by oral gavage. Seven days post gavage, the contents of various locations along the intestinal tract were collected and used for DNA isolation. Illumina sequencing was used to identify the abundance of mutants in the input and output pools based on unique DNA sequences adjacent to the transposon insertion. Mutants depleted from the pool have Tn insertions disrupting genes required for colonization. (B) Plot of genes identified in the input gavage and cecum after 7 days. Gene abundance is standardized by counts per million and each point represents a gene with a Tn insertion. (C) Plot of genes identified in the input gavage and cecum after 7 days. Grey points are Tn insertion sites and coloured points represent Tn insertions in genes required for mucin utilization.
Figure 4:
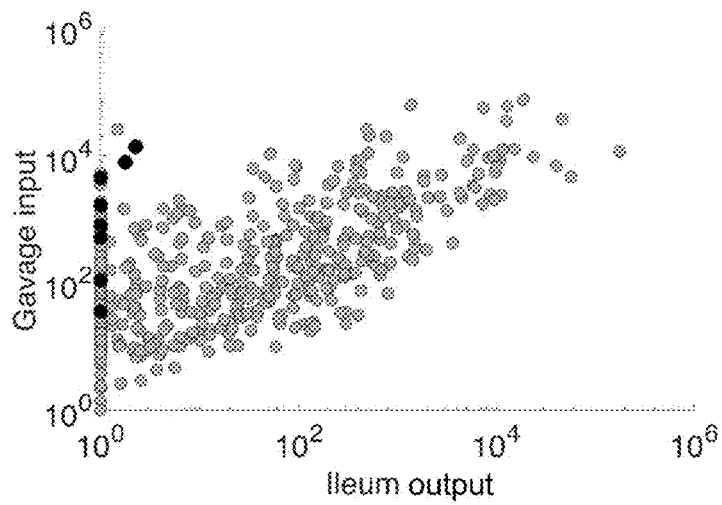
Figure 4:
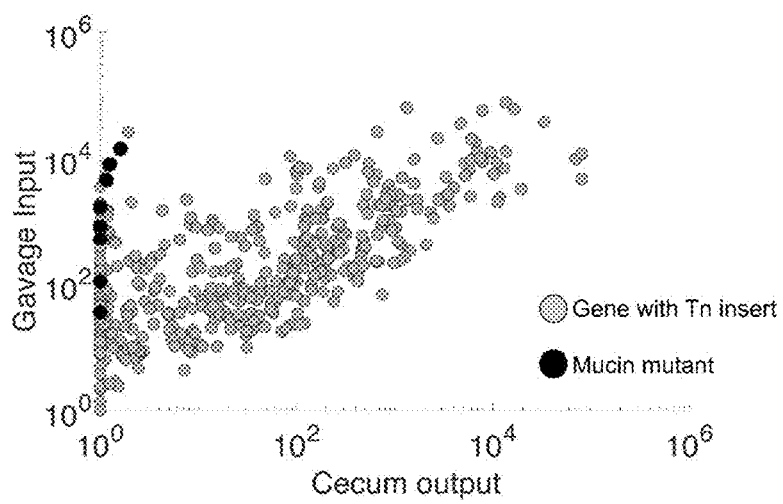

Analysis of the Tn/IN-seq data identified genes required for stable colonization of the intestinal tract (FIG. 4). Genes required for colonization included putative components of the type II secretion system, type IV pili proteins, and glycosyl hydrolases among others (Table 2). Conversely, inactivation of certain genes led to an increased abundance, suggesting that the library could potentially be screen for hypercolonizing variants (Table 3). In addition, mutants unable to grow on mucin were dramatically depleted from the population, confirming that growth on mucin is occurring in vivo and that it is important for *Akkermansia* colonization.

TABLE 2

Representative data of the top 25 genes with decreases in abundance in the cecum seven days post gavage.

| Gene | Accession number protein/gene | SEQ ID Nos (genes) | Annotation | Log2 fold change | Mucin growth |
|---|---|---|---|---|---|
| 'Amuc_0394' | ACD04233/NC_010655.1 (476127 . . . 476885, complement) | SEQ ID NO: 15 | 'type II secretion system protein' | −14.29819088 | No |
| 'Amuc_0544' | ACD04382/NC_010655.1 (642890 . . . 646123, complement) | SEQ ID NO: 16 | 'tetratricopeptide repeat protein' | −12.85004557 | No |
| 'Amuc_1585' | ACD05405/NC_010655.1 (1905728 . . . 1907386, complement) | SEQ ID NO: 17 | 'type II/IV secretion system protein' | −12.36982429 | |
| 'Amuc_1584' | ACD05404/NC_010655.1 (1904390 . . . 1905658, complement) | SEQ ID NO: 18 | 'type II secretion system F family protein' | −11.76964088 | |
| 'Amuc_1102' | ACD04928/NC_010655.1 (1317279 . . . 1317995, complement) | SEQ ID NO: 19 | 'hypothetical protein' | −11.48189687 | |
| 'Amuc_1781' | ACD05599/NC_010655.1 (2169362 . . . 2170345, complement) | SEQ ID NO: 20 | 'MoxR family ATPase' | −10.89820545 | |
| 'Amuc_1486' | ACD05308/NC_010655.1 (1776309 . . . 1776770, complement) | SEQ ID NO: 21 | 'hypothetical protein' | −10.7100209 | No |
| 'Amuc_1443' | ACD05265/NC_010655.1 (1732600 . . . 1733982) | SEQ ID NO: 22 | 'hypothetical protein' | −10.59173905 | No |
| 'Amuc_0775' | ACD04610/NC_010655.1 (913422 . . . 913889, complement) | SEQ ID NO: 23 | 'acyl-CoA thioesterase' | −10.53341842 | |
| 'Amuc_0666' | ACD04503/NC_010655.1 (783434 . . . 784846) | SEQ ID NO: 24 | '3-isopropylmalate dehydratase' | −10.51279975 | |
| 'Amuc_1101' | ACD04927/CP001071.1 (1315394 . . . 1317178, complement) | SEQ ID NO: 25 | 'hypothetical protein' | −10.41174461 | No |
| 'RS01655' | ACD04132/NC_010655.1 (347442 . . . 350402) | SEQ ID NO: 26 | 'glycoside hydrolase family 2' | −10.07979812 | |
| 'Amuc_1914' | ACD05727/NC_010655.1 (2322961 . . . 2324121, complement) | SEQ ID NO: 27 | 'restriction endonuclease subunit S' | −10.0212794 | |
| 'Amuc_2021' | WP_052294492/ NC_010655.1 (2454651 . . . 2455214, complement) | SEQ ID NO: 28 | 'NUDIX domain-containing protein' | −9.969072021 | |
| 'Amuc_0920' | ACD04752/NC_010655.1 (1099438 . . . 1100859) | SEQ ID NO: 29 | 'glycosyl hydrolase family 109 protein 2' | −9.854550941 | |
| 'Amuc_1230' | ACD05055/CP001071.1 (1478807 . . . 1479622, complement) | SEQ ID NO: 30 | 'hypothetical protein' | −9.826157438 | No |
| 'RS02010' | WP_042447573/ NC_010655.1 (423450 . . . 423878, complement) | SEQ ID NO: 31 | 'hypothetical protein' | −9.77626983 | |
| 'Amuc_1558' | ACD05379/NC_010655.1 (1870950 . . . 1872395) | SEQ ID NO: 32 | 'RIP metalloprotease RseP' | −9.751983353 | |
| 'Amuc_0029' | ACD03876/NC_010655.1 (37306 . . . 38232, complement) | SEQ ID NO: 33 | 'dTDP-glucose 4,6-dehydratase' | −9.659119296 | No |

TABLE 2-continued

Representative data of the top 25 genes with decreases in abundance in the cecum seven days post gavage.

| Gene | Accession number protein/gene | SEQ ID Nos (genes) | Annotation | Log2 fold change | Mucin growth |
|---|---|---|---|---|---|
| 'Amuc_0077' | ACD03922/NC_010655.1 (100094 . . . 101293) | SEQ ID NO: 34 | 'glycine C-acetyltransferase' | −9.642209742 | |
| 'Amuc_1974' | ACD05787/NC_010655.1 (2396408 . . . 2399152, complement) | SEQ ID NO: 35 | 'pyruvate, phosphate dikinase' | −9.498736149 | |
| 'RS08560' | WP_012420638/ NC_010655.1 (1926953 . . . 1927837, complement) | SEQ ID NO: 36 | 'DUF3472 domain-containing protein' | −9.464857006 | |
| 'Amuc_0253' | ACD04096/NC_010655.1 (310853 . . . 311722, complement) | SEQ ID NO: 37 | 'M23 family peptidase' | −9.42611747 | |
| 'Amuc_0078' | ACD03923/CP001071.1 (101329 . . . 103947, complement) | SEQ ID NO: 38 | 'PEGA domain-containing protein' | −9.419373842 | |

TABLE 3

Representative data of genes with enhanced abundance in the cecum 7 days post gavage.

| Gene | Accession number protein/gene | Gene SEQ ID NO: | Annotation | Log2 fold change |
|---|---|---|---|---|
| 'Amuc_0996' (AMUC_RS05350) | ACD04824/NC_010655.1 (1188201 . . . 1189811, complement) | SEQ ID NO: 39 | 'ABC transporter ATP-binding protein' | 0.888546921 |
| 'Amuc_1213' | ACD05038/NC_010655.1 (1450497 . . . 1450940) | SEQ ID NO: 40 | 'hypothetical protein' | 1.058687453 |
| 'Amuc_2133' | ACD05942/CP001071.1 (2599892 . . . 2600839) | SEQ ID NO: 41 | 'hypothetical protein' | 1.546616436 |
| 'Amuc_0460' | ACD04298/NC_010655.1 (548882 . . . 549403) | SEQ ID NO: 42 | 'hypothetical protein' | 2.419575989 |
| 'Amuc_0215' | ACD04058/NC_010655.1 (265829 . . . 266431, complement) | SEQ ID NO: 43 | 'PEP-CTERM domain protein' | 2.957572311 |
| 'Amuc_0882' | ACD04715/NC_010655.1 (1052357 . . . 1052686) | SEQ ID NO: 44 | 'hypothetical protein' | 3.707186328 |
| 'Amuc_0922' | ACD04754/NC_010655.1 (1103658 . . . 1105115, complement) | SEQ ID NO: 45 | 'bifunctional metallophosphatase/5"-nucleotidase' | 3.903077196 |
| 'Amuc_1560' | ACD05381/NC_010655.1 (1874068 . . . 1874856) | SEQ ID NO: 46 | 'PEP-CTERM sorting domain-containing protein' | 4.47721439 |

All sequences associated with NCBI protein and gene accession numbers found in the tables are incorporated by reference in their entireties and can be found at www.ncbi.nlm.nih.gov/ [ncbi.nlm.nih.gov]. The genomic sequence of *Akkermansia* can be found under accession number: NC_010655.1, the contents of which are incorporated by reference in its entirety.

REFERENCES

1. Goodman et al. (2011) Nature Protocols. 6(12): 1969-1980
2. Plovier et al. (2017) Nature Medicine 23:107-113
3. Derrien et al. (2004) Int J Syst Evol Microbiol. 54:1469-1476 These references are incorporated in their entireties for details related to the methods described in the examples.

Example 5: *Akkermansia* Interacts with Mucin Layers in Gastrointestinal Track

Figure 5:
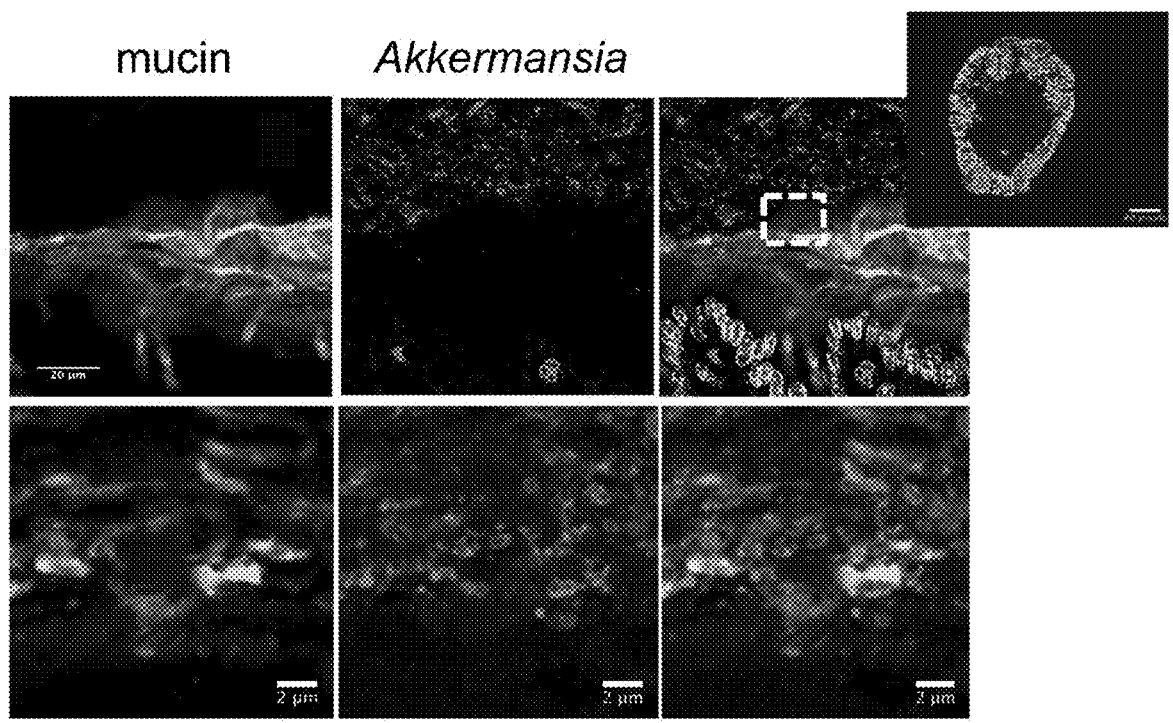
FIG. 5. Representative images of staining of gastrointestinal track of mice for mucin and *Akkermansia*.

Intestinal samples from mice as described in example 4 were taken, sectioned and stained with antibodies against mucin and *Akkermansia*. As shown in FIG. 5, *Akkermansia* is very closely associated with the mucin layer within the intestinal tract.

Figure 6:
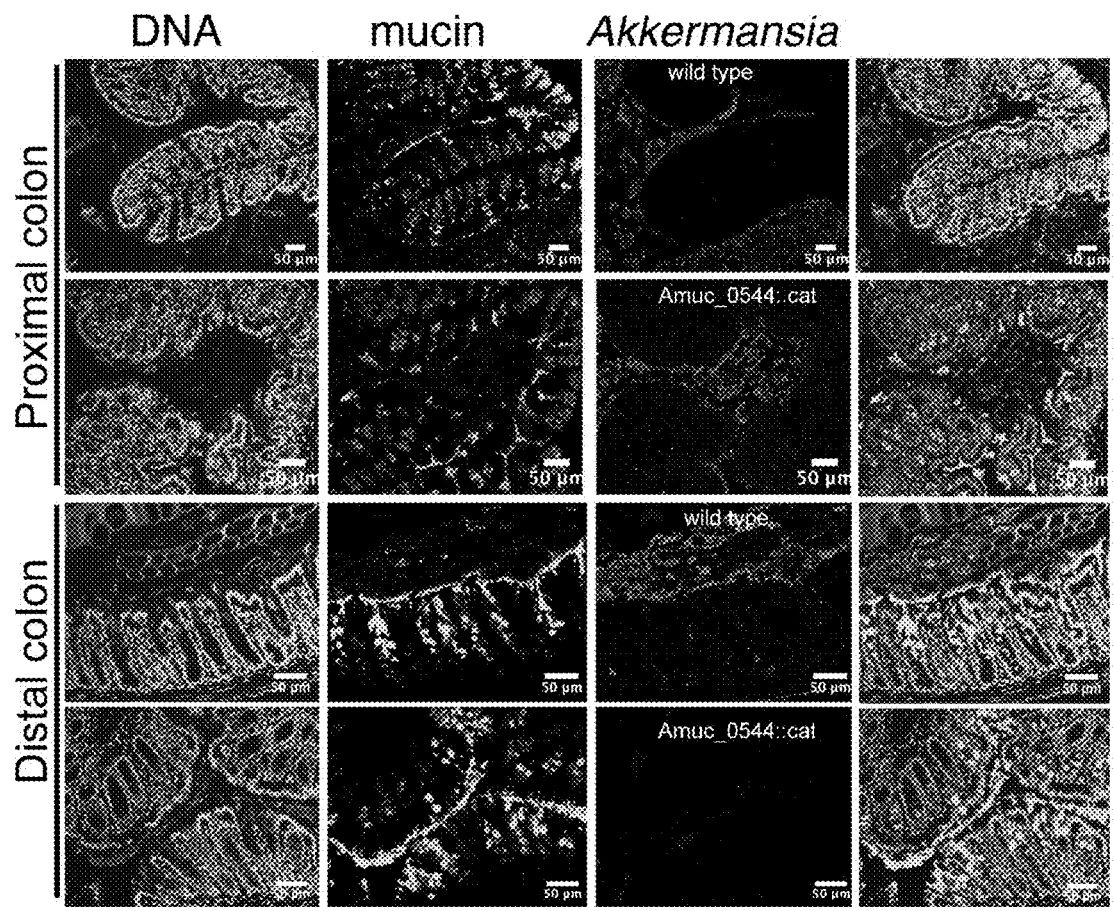
FIG. 6. Representative images of staining of the proximal and distal colon of mice having been colonized with either wild-type (wt) *Akkermansia* or mutant Amuc-0544 *Akkermansia*. As demonstrated in the bottom row, the gene Amuc-0544 is required for the colonization of the distal colon.

Further, the ability of wild-type Akkermansia or mutant Amuc_0544 was also examined in mice. Sections of the proximal and distal colon were obtained, sectioned and stained for mucin or *Akkermansia*. As demonstrated in FIG. 6, while both wt and mutant *Akkermansia* were able to colonize the proximal colon, the gene Amuc-0544 was required for the colonization of the distal colon in mice.

SEQUENCE LISTING

A sequence listing in text format is concurrently submitted with this application and is incorporated in its entirety as part of the application as filed.

The invention claimed is:

1. A method of genetically altering *Akkermansia* bacteria, the method comprising:
   (a) contacting *Akkermansia* bacteria with a transposon vector comprising a transposon in the presence of a transposase, wherein the transposon comprises at least a portion of SEQ ID NO: 47 that is capable of integration into the genome of the *Akkermansia* bacteria, and wherein the transposon comprises a chloramphenicol resistance gene;
   (b) culturing the *Akkermansia* bacteria and the transposase in the presence of chloramphenicol to incorporate the transposon into the genome of the *Akkermansia* bacteria; and
   (c) selecting for genetically altered *Akkermansia* bacteria based on their ability to grow in the presence of the chloramphenicol.

2. The method of claim 1, wherein the transposon comprises the nucleotide sequence of SEQ ID NO: 47.

3. The method of claim 1, wherein the transposon vector comprises the nucleotide sequence of SEQ ID NO: 1.

4. The method of claim 1, wherein step (c) comprises:
   sub-culturing the altered *Akkermansia* bacteria in a medium comprising kanamycin and gentamicin; and
   culturing the altered *Akkermansia* bacteria in the presence of chloramphenicol, gentamicin, and kanamycin.

5. The method of claim 4, wherein the *Akkermansia* bacteria are cultured under anaerobic conditions to select for altered *Akkermansia* that have the incorporated transposon within their genome.

6. The method of claim 1, wherein the method further comprises:
   (d) culturing the plurality of genetically altered *Akkermansia* under conditions to select for a trait; and
   (e) identifying a gene associated with the trait by identifying the gene adjacent to the transposon within the *Akkermansia* genome.

7. The method of claim 6, wherein identifying the gene comprises performing polymerase chain reaction or nucleotide sequencing of the gene.

8. The method of claim 6, wherein the selected trait is utilization of mucin by the *Akkermansia*, and wherein step (b) comprises culturing the genetically altered *Akkermansia* in medium with or without mucin.

9. The method of claim 8, wherein the method further comprises:
   (f) genetically analyzing the genes in the altered *Akkermansia* grown in the presence of mucin and the genes in altered *Akkermansia* grown in the absence of mucin to determine genes that regulate mucin utilization.

10. The method of claim 6, wherein the selected trait is associated with stable colonization of the intestine, and wherein the method further comprises:
    (f) introducing the plurality of genetically altered *Akkermansia* into a subject; and
    (g) detecting the altered *Akkermansia* that have a growth advantage colonizing the intestine of the subject by genetically analyzing the genes in the altered bacteria.

11. The method of claim 10, wherein genetically analyzing the genes is performed by DNA sequencing of at least a portion of the genomes of a plurality of altered *Akkermansia* bacteria.

12. The method of claim 10, wherein the *Akkermansia* bacteria is *Akkermansia muciniphila* bacteria.

13. A genetically altered *Akkermansia* bacteria, wherein the genome of the *Akkermansia* bacteria comprises a transposon comprising at least a portion of SEQ ID NO: 47 and a chloramphenicol resistance gene.

14. The genetically altered *Akkermansia* bacteria of claim 13, wherein the transposon comprises the nucleotide sequence of SEQ ID NO: 47.

15. The genetically altered *Akkermansia* bacteria of claim 13, wherein the bacteria has a disruption of a gene selected from the group consisting of SEQ ID NOs: 2-46.

16. A library of *Akkermansia* bacteria, wherein the library comprises a plurality of the altered *Akkermansia* bacteria of claim 13.

17. The library of claim 16, wherein the library comprises a population of *Akkermansia* bacteria, wherein each bacteria comprises the transposon of SEQ ID NO:47.

18. The library of claim 16, wherein the *Akkermansia* bacteria is *Akkermansia muciniphila* bacteria.

* * * * *